(12) United States Patent
Dong et al.

(10) Patent No.: US 11,104,763 B2
(45) Date of Patent: Aug. 31, 2021

(54) RENEWABLE POLYMERS AND RESINS AND METHODS OF MAKING THE SAME

(71) Applicant: Alliance for Sustainable Energy, LLC, Golden, CO (US)

(72) Inventors: Tao Dong, Lakewood, CO (US); Lieve M. L. Laurens, Denver, CO (US); Philip T. Pienkos, Lakewood, CO (US); Paris Fabian Spinelli, Denver, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 16/483,844

(22) PCT Filed: Apr. 6, 2018

(86) PCT No.: PCT/US2018/026422
§ 371 (c)(1),
(2) Date: Aug. 6, 2019

(87) PCT Pub. No.: WO2018/187667
PCT Pub. Date: Oct. 11, 2018

(65) Prior Publication Data
US 2020/0017638 A1 Jan. 16, 2020

Related U.S. Application Data

(60) Provisional application No. 62/482,238, filed on Apr. 6, 2017.

(51) Int. Cl.
C08G 71/04 (2006.01)
C07C 237/10 (2006.01)
(Continued)

(52) U.S. Cl.
CPC ............ *C08G 71/04* (2013.01); *C07C 237/10* (2013.01); *C07C 237/20* (2013.01);
(Continued)

(58) Field of Classification Search
None
See application file for complete search history.

(56) References Cited

U.S. PATENT DOCUMENTS 2,802,022 A 8/1957 Groszos et al.
3,084,140 A 4/1963 Gurgiolo et al.
(Continued)

FOREIGN PATENT DOCUMENTS

EP 0 152 820 A2 8/1985
EP 0 680 988 A2 11/1995

OTHER PUBLICATIONS

Kochansky ("Structure-Activity Relationships in C-Terminal Fragment Analogs of Pheromone Biosynthesis Activating Neuropeptide in Helicoverpa zea" Archives of Insect Biochemistry and Physiology, 35, 1997, p. 315-322) (Year: 1997).*
(Continued)

*Primary Examiner* — Amy C Bonaparte
(74) *Attorney, Agent, or Firm* — Michael A. McIntyre

(57) ABSTRACT

The present disclosure relates to methods for producing polymers and resins, the method including a first reacting of at least a first diamine with a first carbonate-containing compound and a second carbonate-containing compound to produce at least one of the polymer or the resin, where the first reacting is according to
(Continued)

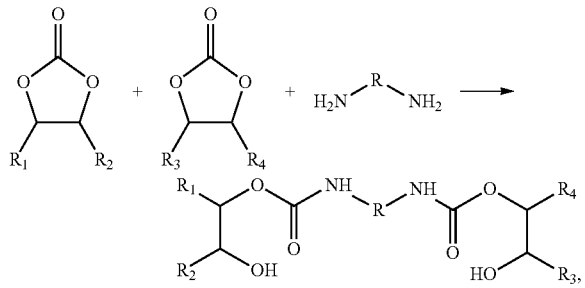

each of $R_1$, $R_2$, $R_3$, and $R_4$ include at least one of a hydrogen atom, a methyl group, a saturated hydrocarbon chain, and/or an unsaturated hydrocarbon chain, and R comprises at least one of a carbon atom, a saturated hydrocarbon chain, and/or an unsaturated hydrocarbon chain.

4 Claims, 17 Drawing Sheets

(51) Int. Cl.
| | |
|---|---|
| C07C 237/20 | (2006.01) |
| C07C 237/22 | (2006.01) |
| C07C 231/02 | (2006.01) |
| C07C 269/04 | (2006.01) |
| C07C 271/16 | (2006.01) |
| C07C 271/20 | (2006.01) |
| C07C 279/12 | (2006.01) |
| C07C 277/08 | (2006.01) |
| C07C 231/12 | (2006.01) |

(52) U.S. Cl.
CPC .......... C07C 237/22 (2013.01); C07C 269/04 (2013.01); C07C 271/16 (2013.01); C07C 271/20 (2013.01); C07C 279/12 (2013.01); C07C 231/02 (2013.01); C07C 231/12 (2013.01); C07C 277/08 (2013.01)

(56) References Cited

U.S. PATENT DOCUMENTS

| | | | |
|---|---|---|---|
| 4,820,830 | A | 4/1989 | Blank |
| 6,838,580 | B2 | 1/2005 | Okada et al. |
| 7,045,577 | B2 | 5/2006 | Wilkes et al. |
| 2007/0111982 | A1* | 5/2007 | Bell ................ A61P 25/04 514/211.06 |
| 2013/0245133 | A1 | 9/2013 | Bezwada |
| 2014/0117280 | A1* | 5/2014 | Ishii ................ B01J 20/2805 252/188.28 |
| 2014/0171535 | A1 | 6/2014 | Narayan et al. |
| 2015/0291741 | A1 | 10/2015 | Narayan et al. |
| 2016/0068630 | A1 | 3/2016 | Carpentier et al. |

OTHER PUBLICATIONS

Esters ("Unusual Amino Acids and Monofluoroacetate from *Dichapetalum michelsonii* (Umutambasha), a Toxic Plant from Rwanda" Planta Med 2013, 79, 334-337) (Year: 2013).*
Pubchem CID 58877832, Create Date Aug. 19, 2012, pp. 1-13.
Pubchem CID 58877833, Create Date Aug. 19, 2012, pp. 1-13.
Pubchem CID 87845413, Create Date Feb. 12, 2015, pp. 1-13.
Begines et al., "Polyurethanes Derived from Carbohydrates and Cystine-Based Monomers", Journal of Applied Polymer Science, 2015, pp. 41304-1-41304-8.
Chung et al., "Synthesis of amino acid-based polymers via atom transfer radical polymerization in aqueous media at ambient temperature", Journal of the Chemical Society, Chemical Communications, 2005, pp. 1046-1048.
Delichatsios, "Novomer. Catalyzing green chemistry.", Watt Now; https://wattnow.org/2011/11/novomer-catalyzing-green-chemistry/, Nov. 15, 2011, pp. 1-3, accessed Aug. 15, 2019.
Hong et al., "High value polyurethane resins from rubber seed oil", Polymer International, 2017, vol. 66, pp. 126-132.
Javni et al., "Polyurethanes from soybean oil, aromatic, and cycloaliphatic diamines by nonisocyanate route", Journal of Applied Polymer Science, 2013, vol. 128, No. 1, pp. 566-571.
Jazi et al., "Synthesis and Applications of Isocyanate Free Polyurethane Materials", Global Journal of Science Frontier Research: B, 2016, vol. 16, No. 3, pp. 1-20.
Kumar et al., "Polyurethanes preparation using proteins obtained from microalgae", Journal of Materials Science, 2014, vol. 49, pp. 7824-7833.
Lee et al., "Green polyurethane from lignin and soybean oil through non-isocyanate reactions", European Polymer Journal, Feb. 2015, vol. 63, pp. 67-73.
Ochiai et al., "Non-isocyanate synthesis and application of telechelic polyurethanes via polycondensation of diurethanes obtained from ethylene carbonate and diamines", Journal of Polymer Science—Part A Polymer Chemistry, 2013, vol. 51, No. 3, pp. 525-533.
Rokicki et al., "A new route to polyurethanes from ethylene carbonate, diamines and diols", Polymer, 2002, vol. 43, pp. 2927-2935.
Tamami et al., "Incorporation of Carbon Dioxide into Soybean Oil and Subsequent Preparation and Studies of Nonisocyanate Polyurethane Networks", Journal of Applied Polymer Science, 2004, vol. 92, pp. 883-891.
Ubaghs et al., "Polyurethanes with Pendant Hydroxyl Groups: Synthesis and Characterization", Macromolecular Rapid Communications, 2004, vol. 25, No. 3, pp. 517-521.
Zhang et al., "Non-isocyanate poly(amide-hydroxyurethane)s from sustainable resources", Green Chemistry, 2016, vol. 18, No. 17, pp. 4667-4681.
Zia et al., "Alginate based polyurethanes: A review of recent advances and perspective", International Journal of Biological Macromolecules, 2015, vol. 79, pp. 377-387.
International Search Report and Written Opinion, International Application No. PCT/US18/26422, dated Jul. 16, 2018, pp. 1-10.

* cited by examiner

RENEWABLE POLYMERS AND RESINS AND METHODS OF MAKING THE SAME

CROSS-REFERENCE TO RELATED APPLICATIONS

This application claims the benefit of U.S. Provisional Patent Application No. 62/482,238 filed Apr. 6, 2017, the contents of which are incorporated herein by reference in their entirety.

CONTRACTUAL ORIGIN

The United States Government has rights in this disclosure under Contract No. DE-AC36-08GO28308 between the United States Department of Energy and Alliance for Sustainable Energy, LLC, the Manager and Operator of the National Renewable Energy Laboratory.

BACKGROUND

Polyurethane (PU) is a polymer joined by carbamate (urethane) linkages between polyols (typically containing at least two functional groups, e.g. dipropylene glycol) and isocyanate electrophilic linkers (ideally two isocyanate groups per linker). PU polymers are traditionally and most commonly formed by reacting a di- or polyisocyanate with a polyol, with both varying in composition and structure (e.g. glycerol, sorbitol, sucrose, etc. as the polyol and toluene di-isocyanate and methyl diphenyl di-isocyanate as common aromatic isocyanate linkers). The production of traditional isocyanates follows a toxic synthesis route of treating amines with phosgene and produces hydrochloric acid. Since isocyanates are highly toxic, it would be advantageous to replace them with nontoxic and renewable molecules. Thus, there remains a need for environmentally friendly, bio-derived, renewably-sourced polymers and resins and methods for making these materials. In addition, for the production of polyurethane foams, long-chain polyols are desirable and bio-derived polyunsaturated fatty acids (PUFA) form excellent feedstocks. Because the reactivity of the polyurethane synthesis is linked with the number of hydroxyl functionalities of the polyol, it is thought that the higher level of unsaturation of the fatty acids leads to stronger polymers and therefore enriching oils for higher level of PUFA will help to increase the reactivity of the resulting polyols. Traditional and commercial purification strategies for producing enriched PUFA feedstocks to produce polyols, are often based on costly and time intensive chromatography-based separations, which, because of the high costs, are limited to applications having very pure starting mixtures and do not lend themselves well for low-cost polymer applications. Alternative common enrichment strategies such as urea complexation or winterization (e.g. selective crystallization of saturated fatty acids) are used at scale, however, enrichment via these strategies are either not practical, not effective or too costly at scale. The chromatography-based separations are hindered by rapid fouling of membranes and resins used when treating less-pure feed streams. A scalable and cost-effective approach for PUFA enrichment is needed.

SUMMARY

An aspect of the present disclosure is a composition that includes

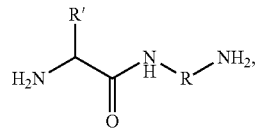

where R is a first hydrocarbon group and R' is a second hydrocarbon group.

In some embodiments of the present disclosure, the composition may further include

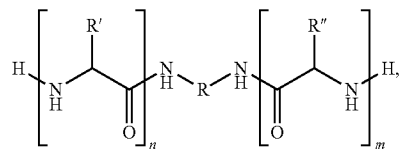

where R" may be a third hydrocarbon group. In some embodiments of the present disclosure, R, R', and R" may each include at least one of a saturated hydrocarbon chain and/or an unsaturated hydrocarbon chain having between 1 and 100 carbon atoms. In some embodiments of the present disclosure, R may further include at least one of a hydroxyl group, an amine group, an aryl group, an aromatic ring structure, a carboxyl group, ketone, and/or a sulfur-containing group.

In some embodiments of the present disclosure, the composition may include at least one of

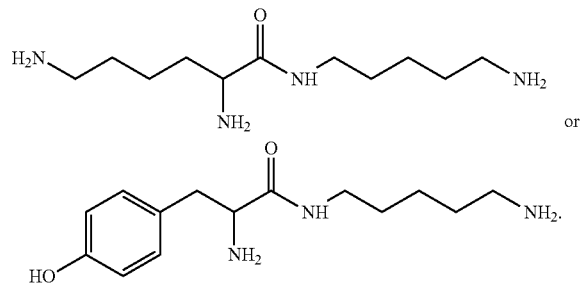

An aspect of the present disclosure is a composition that includes

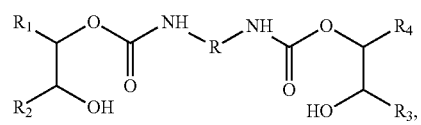

where each of $R_1$, $R_2$, $R_3$, and $R_4$ includes at least one of at least one of a hydrogen atom, a methyl group, a saturated hydrocarbon chain, and/or an unsaturated hydrocarbon chain, and R comprises at least one of a carbon atom, a saturated hydrocarbon chain, and/or an unsaturated hydrocarbon chain. In some embodiments of the present disclosure, at least one of $R_1$, $R_2$, $R_3$, and $R_4$ may have between 1 and 100 carbon atoms. In some embodiments of the present disclosure, at least one of $R_1$, $R_2$, $R_3$, and $R_4$ may include at least one of a branched chain or a straight chain. In some embodiments of the present disclosure, R may further include at least one of a hydroxyl group, a carboxylic acid group, an amine group, a benzene ring, a phenol group, an amide group, an indol group, an imidazole group, a sulfhydryl group, and/or a guanidinium group.

In some embodiments of the present disclosure, R may further include

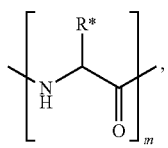

m may be between 1 and 30, and R* may include at least one of a hydrogen atom, a carbon atom, a methyl group, an alkane, an alkene, and/or an alkyne. In some embodiments of the present disclosure, R* may further include at least one of a hydroxyl group, a carboxylic acid group, an amine group, a benzene ring, a phenol group, an amide group, an indol group, an imidazole group, a sulfhydryl group, and/or a guanidinium group.

In some embodiments of the present disclosure, at least one of $R_1$, $R_2$, $R_3$, and $R_4$ may further include a functional group A having the structure

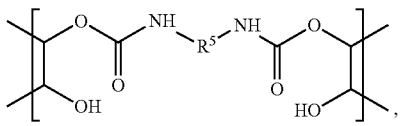

where $R^5$ may include at least one of a carbon atom, a —$CH_2$— group, an alkane, an alkene, or an alkyne.

In some embodiments of the present disclosure, R may include at least one of

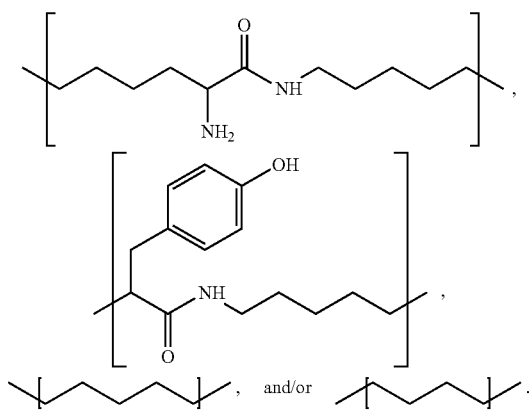

In some embodiments of the present disclosure, at least one of $R_1$, $R_2$, $R_3$, and $R_4$ may further include a functional group A having the structure

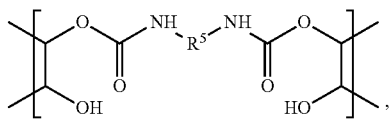

where $R^5$ may nclude at least one of a —$CH_2$— group, an alkane, an alkene, and/or an alkyne.

In some embodiments of the present disclosure, $R_1$ and $R_2$ may have a combined total number of carbons atoms between 14 and 18. In some embodiments of the present disclosure, the combined total number of carbons atoms of $R_1$ and $R_2$ may include between zero and four of functional group A. In some embodiments of the present disclosure, $R_3$ and $R_4$ may have a combined total number of carbons atoms between 14 and 18. In some embodiments of the present disclosure, the combined total number of carbon atoms of $R_3$ and $R_4$ may include between zero and four of functional group A. In some embodiments of the present disclosure, the composition may have a break stress between 1 MPa and 30 MPa.

An aspect of the present disclosure is a method for producing polymers and resins, the method including a first reacting of at least a first diamine with a first carbonate-containing compound and a second carbonate-containing compound to produce at least one of the polymer or the resin, where the first reacting is according to

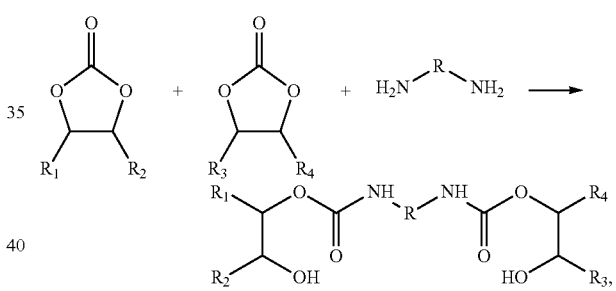

each of $R_1$, $R_2$, $R_3$, and $R_4$ include at least one of a hydrogen atom, a methyl group, a saturated hydrocarbon chain, and/or an unsaturated hydrocarbon chain, and R comprises at least one of a carbon atom, a saturated hydrocarbon chain, and/or an unsaturated hydrocarbon chain.

BRIEF DESCRIPTION OF THE DRAWINGS

Exemplary embodiments are illustrated in referenced figures of the drawings. It is intended that the embodiments and figures disclosed herein are to be considered illustrative rather than limiting.

REFERENCE NUMBERS

Figure 1:
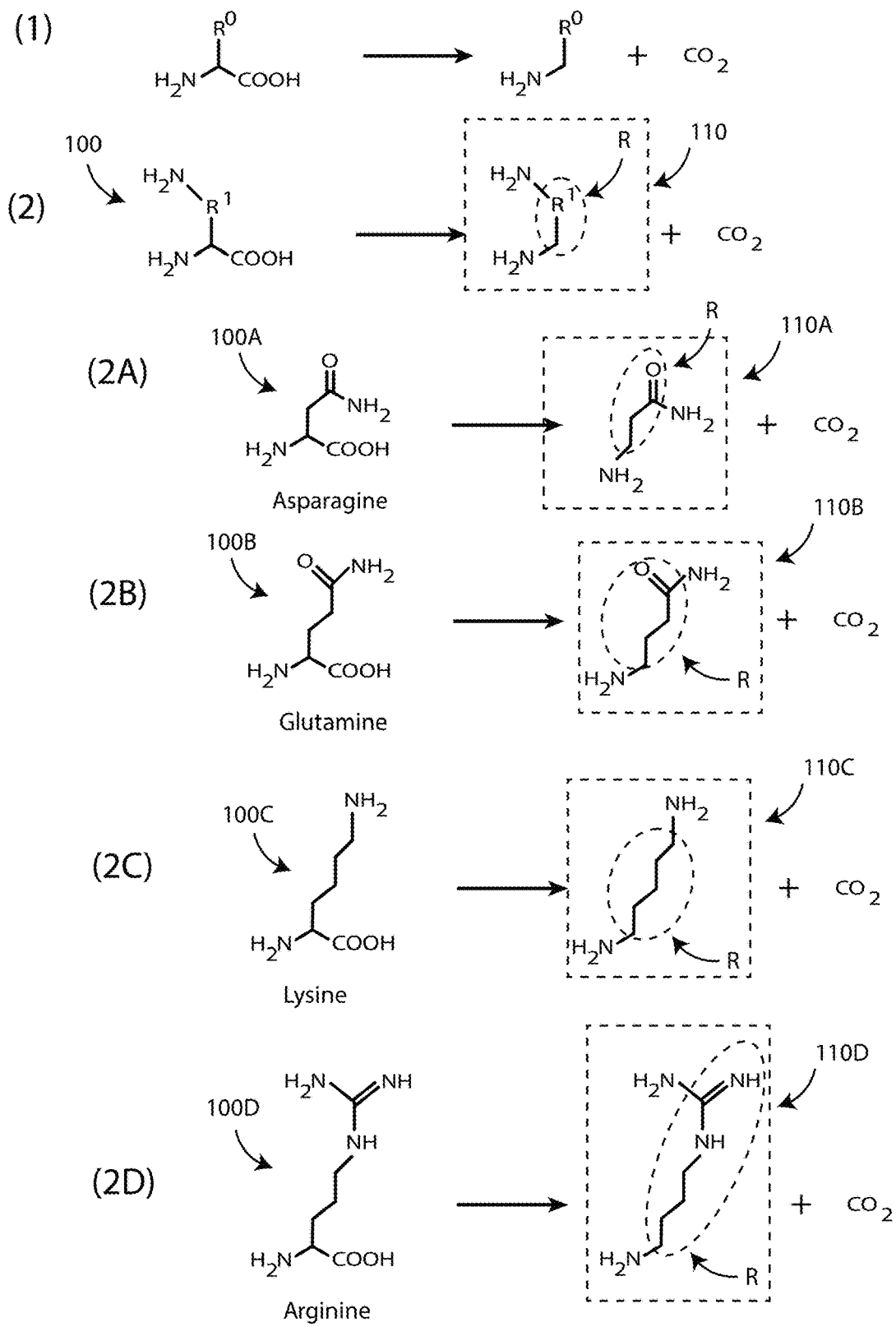
FIG. 1 illustrates decarboxylation reactions of amino acids to produce diamine cross-linking molecules, according to some embodiments of the present disclosure.

100 . . . amino acid
110 . . . diamine
200 . . . extended diamine
300 . . . first lipid
310 . . . fatty acyl chain having a carbonate group
320 . . . carbonate group
330 . . . molecule (e.g. polymer and/or resin)
400 . . . second lipid
410 . . . fatty acyl chain having an epoxy group
420 . . . epoxy group
500 . . . third lipid
510 . . . fatty acyl chain having a carbon-carbon double bond
520 . . . carbon-carbon double bond
700 . . . process
710 . . . biomass source
715 . . . biomass
720 . . . first separation unit
722 . . . amino acid mixture
724 . . . lipid mixture
730 . . . second separation unit
732 . . . first amino acid
734 . . . $n^{th}$ amino acid
736 . . . second byproduct
740 . . . third separation unit
742 . . . unsaturated fatty acid
744 . . . saturated fatty acid and derivatives
750 . . . upgrading
760 . . . polymer/resin
800 . . . decarboxylation reactor
802 . . . diamine
810 . . . cross-linker extension reactor
812 . . . extended diamine
820 . . . epoxidation reactor
825 . . . epoxidized fatty acid (epoxidized lipid)
830 . . . carbonating reactor
835 . . . carbonated fatty acid (carbonated lipid)
840 . . . polymerization and/or resin reactor

DETAILED DESCRIPTION

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

The present disclosure relates to petroleum-derived and/or biomass-derived polymers and/or resins and methods for making these polymers and/or resins, which, among other advantages, may eliminate or reduce the use of toxic isocyanates. For example, according to some embodiments of the present disclosure, polymers and/or resins may be produced using amino acids, peptides, polyamines, and/or polypeptides and carbonated lipids (also referred to herein as oils) such as triglycerides, diglycerides, monoglycerides and/or fatty acids derivatives and other compounds having two or more carbonated functional groups. Amino acids can be produced by fermentation or obtained from waste resources, such as agriculture waste. One source of amino acids is the residue of a processing route involving microalgae. The protein content of microalgae may be up to 50% of the biomass, with the majority of the protein enriched in a post-extraction residue. The protein fraction may be used as precursors to produce diamines and/or polyamines. Amino acid derived diamines may be produced by the decarboxylation of amino acids such as at least one of lysine, arginine, histidine, and/or any other suitable amino acid and/or peptide. The decarboxylation may be carried out via enzymatic and/or catalytic methods. In some embodiments of the present disclosure, diamines and/or polyamines may be produced by reaction of an amino acid with an amine molecule (e.g. 1,5-diaminopentane, 1,12-diaminododecane and/or 1,2-diaminoethane). Similarly, peptide-derived diamines and polyamines may be produced by the reaction of a peptide with a diamine molecule. A diamine molecule (e.g. 1,12-diaminododecane) may bond to the carboxylic terminus of an amino acid and/or peptide molecule to form an amino acid and/or a peptide-derived di(poly)amine. For the example of a reaction starting with amino acids, if the starting amino acid is lysine, arginine, and/or histidine, a polyamine may be produced by this reaction. For the example of a reaction starting with peptides, if there is lysine, arginine, and/or histidine in the peptide molecule, a peptide-derived polyamine may be produced. Otherwise, an amino acid (peptide)-derived diamine may be produced. In addition, the amino acids, peptides, and/or polypeptides described herein may be of either chiral form, e.g. L-configurations and/or D-configurations.

These amino acid (and peptide)-derived diamines (and polyamines; e.g. triamines and/or amines containing more than three amine functional groups) may react with (e.g. crosslink) carbonated lipids (e.g. oils), including triglycerides, fatty acids and/or any compound having two or more carbonate groups to form polymers and/or resins. Physical and chemical properties of the resultant polymers and/or resins will vary with the composition of the amino acid (and peptide)-derived diamines (and polyamines). Thus, using the materials and methods described herein, a wide range of polymers and/or resins may be designed and produced having a broad spectrum of physical properties and/or performance metrics. Lipids (e.g. oils) include but are not limited to triglycerides, diglycerides, monoglycerides, phospholipids, glycolipids, free fatty acids, fatty acid salts, fatty acid derived fatty alcohols, and hydroxyl fatty acids. In some embodiments of the present disclosure, compounds having two or more unsaturated double bonds, e.g. carbon-carbon double bonds, may be used to produce carbonated molecules that may be reacted as described herein, with cross-linking molecules (e.g. diamines) to produce novel resins and/or polymers. An example of a compound having two or more saturated double bonds that may be suitable for some embodiments of the present disclosure is butadiene.

The present disclosure also relates to methods for producing these bio-derived polymers and/or resins, including methods for producing and/or separating the reactants used to make them. For example, cost-effective purification and/or selective upgrading of polyunsaturated fatty acids (PUFA) may enable the development of cost-effective processes for making bio-derived polymers and/or resins. In some embodiments of the present disclosure electrophoresis may be implemented to achieve the separation and/or fractionation of crude oils, resulting in an up to 6-fold enrichment of PUFAs, to a purity of >98% PUFA in the resulting fatty acid composition. Thus, electrophoresis methods as described herein may be well suited for processing crude oils, such as those derived from algae, where the complex nature of the oils does not meet the high-purity requirement for traditional purification strategies, e.g. chromatography-based. In addition, electrophoresis-driven purification routes as described herein may be scaled up to large reactor systems and may be set up as an on-line purification and/or fractionation system (as opposed to a batch process), enabling the production of different product streams isolated from a single oil source. Thus, some embodiments of the separation methods, systems, and/or strategies described herein may provide significant benefits to commercial PUFA producers (and/or other polymer and/or resin producers), as well as those who aim to develop a biorefinery facility where PUFAs could be produced as a side-stream from oils, with at least a portion of the remaining biomass-derived components upgraded to fuels and/or chemicals.

In some embodiments of the present disclosure a selective deoxygenation process may be implemented to achieve the separation and/or fractionation of crude oils, resulting in enrichment of PUFAs in unreacted free fatty acid stream. Thus, some embodiments of the present disclosure relate to a method to selectively deoxygenate saturated free fatty acids into alkanes, while keeping polyunsaturated fatty acid (PUFA) in their free fatty acid (FFA) form during the reaction. Thus, PUFAs can be separated from hydrocarbons after the reaction due to the different physical-chemical properties of alkanes and FFA. The selective deoxygenation may be implemented by using a shape-selective catalyst embedded with at least one of palladium, nickel, and/or platinum. By choosing the proper cut-off size of pore diameter of shape-selective catalyst only straight chain saturated fatty acids can enter the microporous structure of the catalyst matrix to be deoxygenated by the embedded metal catalysts, while PUFAs, which have a long and curved carbon chain (due to an extensive number of cis double bonds) will not be able to enter the catalyst pores. After the reaction, alkanes produced via deoxygenation are distinct from PUFAs in chemical structure. PUFA and produced alkanes can be readily separated via known approaches, such as ion-exchange chromatography or distillation after the reaction. The method is expected to be cost-effective and scalable for large amount of PUFA production. In this process alkanes can be produced as a coproduct, which can be used as a green diesel blendstock.

There are twenty naturally occurring amino acids, which may be used as described herein to produce cross-linking molecules to be reacted with other molecules to produce polymers and/or resins. The twenty naturally occurring amino acids are glycine, alanine, serine, threonine, cysteine, valine, leucine, isoleucine, methionine, proline, phenylalanine, tyrosine, tryptophan, aspartic acid, glutamic acid, asparagine, glutamine, histidine, lysine, and arginine. These can all be described, as well as other amino acids, by the general structure,

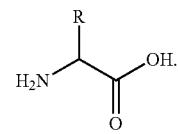

In addition to the twenty naturally occurring amino acids, other bio-derived amine-containing compounds, such as gamma-aminobutyric acid (γ-aminobutyric acid), and/or 2,6-diaminopimelic acid may be utilized according to some of the embodiments described herein, either in place of the 20 naturally occurring amino acids and/or in addition to the 20 naturally occurring amino acids.

Thus, the R-group of the general amino acid structure shown above may be any desirable functional group, including hydrogen, an alkyl group (linear and/or branched), a hydroxyl group, an amine group, an aryl group, an unsaturated hydrocarbon group (one or more aromatic ring structures, linear and/or branched), a carboxyl group, and/or a sulfur-containing. Further, as described herein, two or more amino acids may be reacted according to Reaction (1) below to form at least one peptides and/or polypeptide by reacting the amine functional group of a first amino acid, peptide, and/or polypeptide, with the hydroxyl function group of a second amino acid, peptide, and/or polypeptide, resulting in the following general structures for peptides and/or polypeptides:

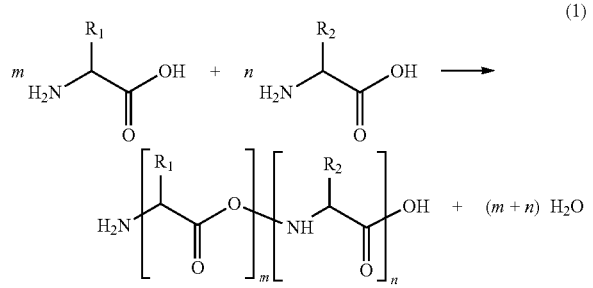

(1)

Referring to Reaction (1), the resultant peptide and/or polypeptide may be a randomly distributed mixture of two or more amino acid repeat units and/or a non-random distribution of two or more amino acid repeat units; e.g. ABAB, AABB, and/or any other suitable block copolymers. m refers to the number of repeat units of the first repeat unit contained in the peptide and/or polypeptide and n refers to the number of repeat units of the second repeat unit contained in the peptide and/or polypeptide. In some embodiments of the present disclosure, at least one of m and/or n may be between 0 and 30.

Other important reactants, according to some embodiments of the present disclosure, include diamines, which have the following general structure:

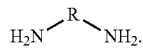

The R-group of the general diamine structure shown above may be any desirable organic functional group, including alkanes, alkenes, and/or alkynes (e.g. saturated and/or unsaturated organic functional groups), that are branched and/or straight-chained. In addition, the R-group of a diamine may be further functionalized with at least one of a hydroxyl group, an amine group, an aryl group, an unsaturated hydrocarbon group (one or more aromatic ring structures, linear and/or branched), a carboxyl group, ketone, and/or a sulfur-containing group.

Other important reactants, according to some embodiments of the present disclosure, include compounds having unsaturated carbon chains, for example, straight-chained and/or branched hydrocarbon chains having at least one carbon-carbon double bond. Examples include compounds having unsaturated fatty acid chains having the general structure,

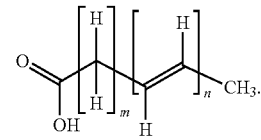

In some embodiments of the present disclosure, the structure above may be more generally represented as an olefin, a hydrocarbon chain, having one or more carbon-carbon double bonds, where the end-groups may be represented by R, where R may include at least one of a hydrogen atom, a methyl group, a carboxylic acid group, and/or an —SH group. This more general structure may be represented by,

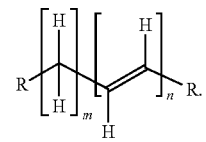

For both examples, the fatty acid chain and an olefin, both the m repeat unit and the n repeat unit may be randomly distributed along the chain, or may be distributed along the chain in some repeat pattern; e.g. ABAB, or AABBAABB, etc.

Taking a fatty acid molecule as an example, a fatty acid chain may terminate at one end with a carboxylic acid end-group and at a second end with a methyl group. In between these two end-groups, an unsaturated fatty acid chain may have at least one carbon-carbon double bond (e.g. $n \geq 1$). In some embodiments of the present disclosure, n may equal 1, 2, 3, or 4. An unsaturated fatty acid chain may include a number of —$CH_2$— repeat units, where m represents the number of repeat units. In some embodiment of the present disclosure, m may be between 1 and 100. As used herein a saturated fatty acid chain only contains repeat units, —$CH_2$—, connected by single bonds (e.g. no double and/or triple bonds). In other words, n=0 for saturated acyl chain.

Referring to the fatty acid structure above, as used herein, a fatty acid chain includes a carboxyl group and a fatty acyl chain. Thus, a fatty acyl chain is defined herein as a linear carbon chain and/or branched carbon chain having between 2 and 50 carbon atoms or between 4 and 30 carbon atoms, where m+n is between 2 and 50 and/or between 4 and 30. A fatty acyl group may be saturated or unsaturated. As will be described below, an acyl group may have other functional groups including epoxy groups, acrylate and/or carbonate groups, hydroxyl groups, ketone groups, aromatic groups.

There are a number of compounds (e.g. molecules) that contain acyl chains that may be used, according to some of the embodiments of the present disclosure, to form novel polymers and/or resins, including a variety that are bio-derived and/or bio-sourced. These include at least one of soybean oils, linseed oils, castor oils, and various oils derived from algae, including algae from the genera *Chlorella, Scenedesmus*, and/or *Nannochloropsis*. Table 1 below summarizes the composition of various bio-derived oils in terms of their composition (weight percent) of various fatty acyl chain lengths and the number of carbon-carbon double bonds (CX:Y where CX is the chain length as total number of carbon bonds and Y is the number of carbon-carbon double bonds). The composition of the oils, with respect to the fatty acid unsaturation is related to the reactivity of the molecules in the polymer/resin synthesis reaction scheme described herein.

to produce a diamine 110C and $CO_2$; and Reaction 2D illustrates the decarboxylation of arginine 100D to produce a diamine 110D and $CO_2$. Thus, in some embodiments of the present disclosure, at least one of an amino amide, an alkyl diamine, and/or an alkyl guanidine may be produced by the

TABLE 1

Fatty Acid Profiles for Some Feedstocks

| oil | C14:0 | C16:0 | C16:1 | C16:2 | C16:3 | C16:4 | C18:0 | C18:1 | C18:2 |
|---|---|---|---|---|---|---|---|---|---|
| soybean | | 11.3 | 0.1 | | | | 3.6 | 24.9 | 53.0 |
| linseed | | 6.0 | | | | | 2.5 | 19.0 | 24.1 |
| castor | | 1.4 | | | | | 1.2 | 5.9 | 5.7 |
| algae: *Chlorella* sp. | 1.1 | 23.5 | 4.7 | 2.4 | 6.0 | 2.9 | 1.7 | 18.2 | 22.2 |
| algae: *Scenedesmus* sp. | 1.6 | 13.2 | 4.0 | 3.1 | 2.1 | 1.2 | 3.5 | 46.8 | 8.0 |
| algae: *Nannochloropsis* sp. | 6.0 | 37.1 | 33.6 | 0.0 | 0.2 | 0.0 | 0.6 | 11.8 | 1.4 |

| oil | C18:3 | C18:4 | C20:0 | C20:1 | C20:4 | C20:5 | C22:0 | C22:1 | C24:0 | $C_{18}H_{34}O_3$ Ricinoleic acid |
|---|---|---|---|---|---|---|---|---|---|---|
| soybean | 6.1 | | 0.3 | 0.3 | | | | 0.3 | 0.1 | |
| linseed | 47.4 | | 0.5 | | | | | | | |
| castor | 0.7 | | 0.1 | | 0.5 | | | | | 84.4 |
| algae: *Chlorella* sp. | 16.4 | 0.0 | 0.2 | 0.1 | 0.0 | 0.0 | | | | |
| algae: *Scenedesmus* sp. | 9.5 | 1.4 | 0.3 | 1.2 | 0.4 | 0.6 | | | | |
| algae: *Nannochloropsis* sp. | 0.3 | 0.0 | 0.1 | 0.0 | 1.5 | 5.9 | | | | |

Thus, referring to Table 1, some oils derived from the algae *Nannochloropsis* may contain about 5.9 weight percent of an oil constituent having an average chain length of about 20 (m+n) with an average number of 5 carbon-carbon double bonds, also referred to as C20:5. Since the example oils summarized in Table 1 are typically triglycerides, Table 2 below summarizes typical numbers for the quantity of double bonds present per triglyceride molecule, as well as the number of double bonds present per fatty acyl chain.

TABLE 2

Typical Number of Double Bonds for Some Feedstocks

| Oil | Double bonds per triglyceride | Double bonds per fatty acyl chain |
|---|---|---|
| soybean | 4.46 | 1.49 |
| Linseed | 6.30 | 2.10 |
| Castor | 3.18 | 1.06 |
| Chlorella | 4.50 | 1.50 |
| Scenedesmus | 3.72 | 1.24 |
| Nannochloropsis | 2.43 | 0.81 |

FIG. 1 summarizes examples of decarboxylation reactions for decarboxylating amino acids 100 to produce amines and/or diamines 110. As described herein, diamines 110 may be directly used as cross-linkers in reactions with lipids and/or molecules containing at least one acyl chain to produce useful polymers and/or resins. Reaction 1 of FIG. 1 illustrates the general decarboxylation reaction of an amino acid having only one amine functional group. Reaction 2 of FIG. 1 shows a generic structure for a diamine 110 resulting from the decarboxylation of an amino acid 100. Reactions 2A through 2D of FIG. 1 illustrate specific examples where the carboxyl groups of asparagine, glutamine, lysine, and arginine are removed (decarboxylated) to produce diamines and carbon dioxide ($CO_2$). Reaction 2A illustrates the decarboxylation of asparagine 100A to produce a diamine 110A and $CO_2$; Reaction 2B illustrates the decarboxylation of glutamine 100B to produce a diamine 110B and $CO_2$; Reaction 2C illustrates the decarboxylation of lysine 100C decarboxylation of at least one of asparagine, glutamine, lysine, and/or arginine, such that at least one of the amino amide, the alkyl diamine, and/or the alkyl guanidine may be used in subsequent reactions to cross-link lipids and/or any other suitable compound containing at least one fatty acyl chain having at least one carbon-carbon double bond to produce useful polymers and/or resins.

Referring again to FIG. 1, Reaction 2 and Reactions 2A through 2D show that all of the example diamine cross-linking molecules shown (110A, 110B, 110C, and 110D) may be simplified to represent an R group positioned between two amine groups, as shown above for a diamine. Thus, an R group may include at least one of a saturated hydrocarbon chain (branched and/or linear) and/or an unsaturated hydrocarbon chain (branched and/or linear), where such hydrocarbon chains may have a variety of elements inserted into the chain (e.g. nitrogen, sulfur and/or may have a variety of functional groups attached to the hydrocarbon chains including oxygen functional groups, amine groups, and/or aromatic ring structures.

Figure 2:
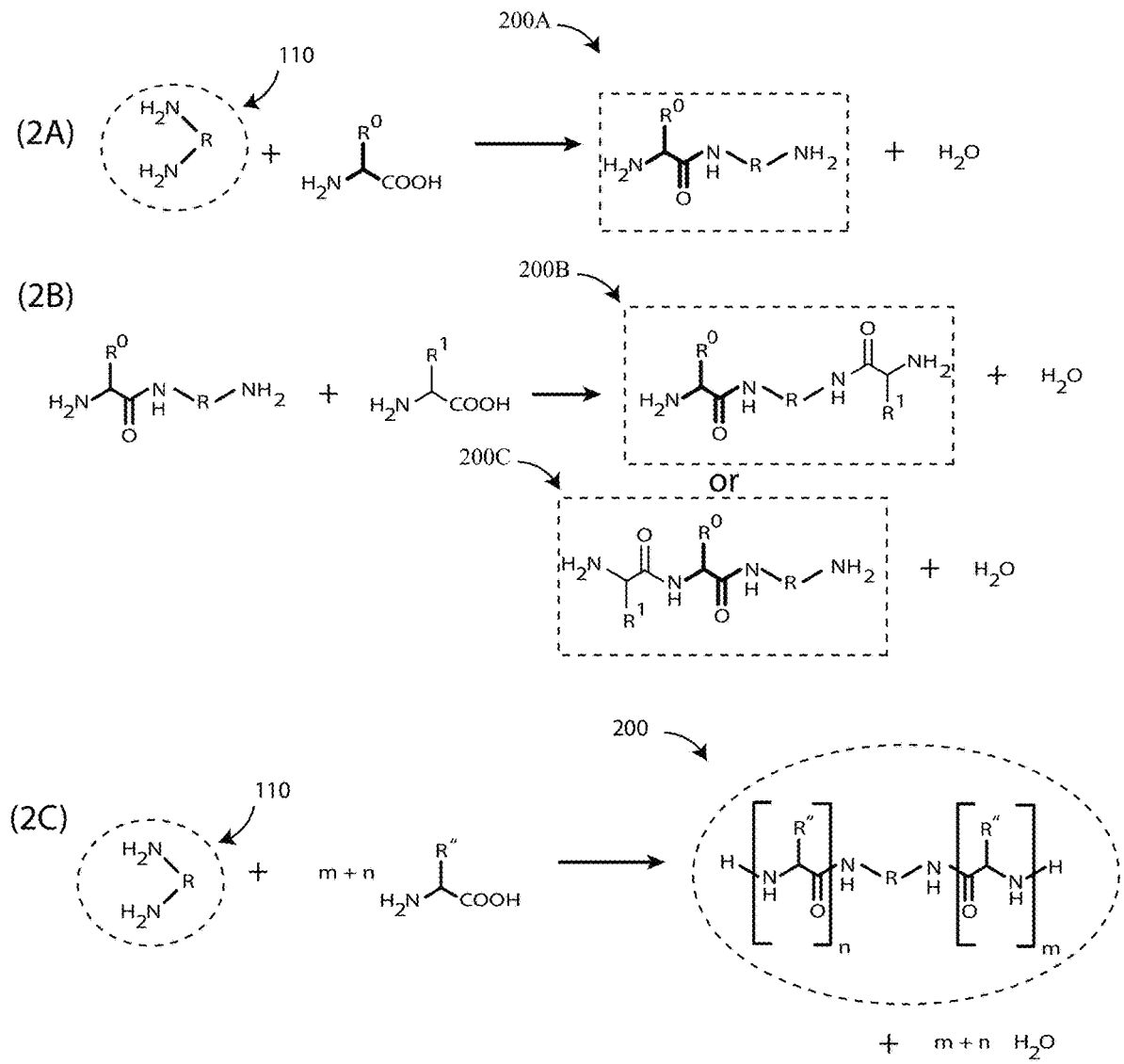
FIG. 2 illustrates chain extension reactions for producing diamine cross-linking molecules larger than single amino acids, according to some embodiments of the present disclosure.

FIG. 2 illustrates that a diamine 110 resulting for example from the decarboxylation of an amino acid (see FIG. 1) may be reacted with at least one amino acid, in at least one reaction step, to produce extended diamines 200 having larger molecular weights than the starting diamine 110. Amino acids do not need to be the α-amino acids common to proteins but could also be omega-amino acids such as gamma-aminobutyrate and/or others. Thus, as shown in Reaction 2A, a starting diamine 110 may be reacted with an amino acid (heavy line) to form a first extended diamine 200A, by reacting one of the amine groups of the starting diamine 110 with the carboxyl group of the amino acid, creating a peptide bond and water. As shown in Reaction 2B, the first extended diamine 200A may reacted with another amino acid (light line) to further extend the chain length of the first extended diamine 200A to produce a second extended diamine, either 200B and/or 200C, depending on which amine group of the first extended diamine 200A reacts with the amino acid shown in Reaction 2B. Thus, Reaction 2C generalizes Reactions 2A and 2B and illustrates that a starting diamine 110 may be reacted with one or more amino acids (m+n) to form an extended diamine 200 having (m+n) peptide bonds and (m+n) water. If a diamine reacts with an amino acid or peptide contains lysine/histidine/arginine, then a polyamine (with 3 or more amine groups) will be formed. As described herein, a polyamine can also behave as a cross linker to react with several carbonated fatty acids to produce useful polymers and/or resins. Referring again to FIG. 2, Reactions 2A through 2C show that the diamine cross-linking molecules shown 110 may be simplified to represent an R group positioned between two amine groups, as shown above for a diamine. Thus, an R group may include at least one of a saturated hydrocarbon chain (branched and/or linear) and/or an unsaturated hydrocarbon chain (branched and/or linear), where such hydrocarbon chains may have a variety of elements inserted into the chain (e.g. nitrogen, sulfur and/or may have a variety of functional groups attached to the hydrocarbon chains including oxygen functional groups, amine groups, and/or aromatic ring structures. Generally, the reactions described herein, and the resultant polymers and/or resins may be fabricated using any organic compound having at least two amine functional groups. Thus, any primary, secondary, and/or tertiary amine having at least two amine functional groups may be used according to the reactions shown in FIG. 2 and described below.

Figure 3:
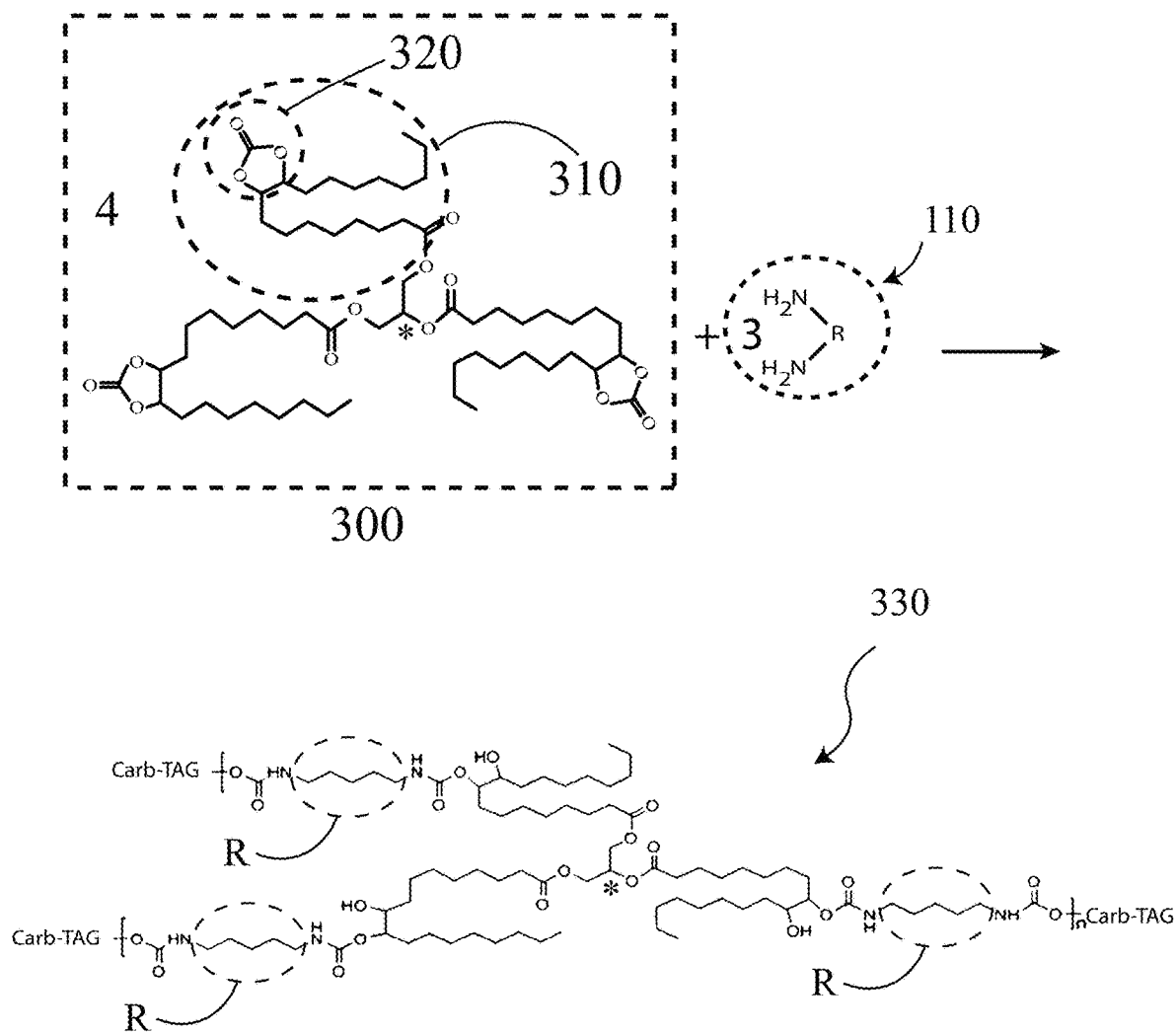
FIG. 3 illustrates a reaction for reacting a lipid with a diamine molecule to form a polymer and/or resin, according to some embodiments of the present disclosure.
Figure 4:
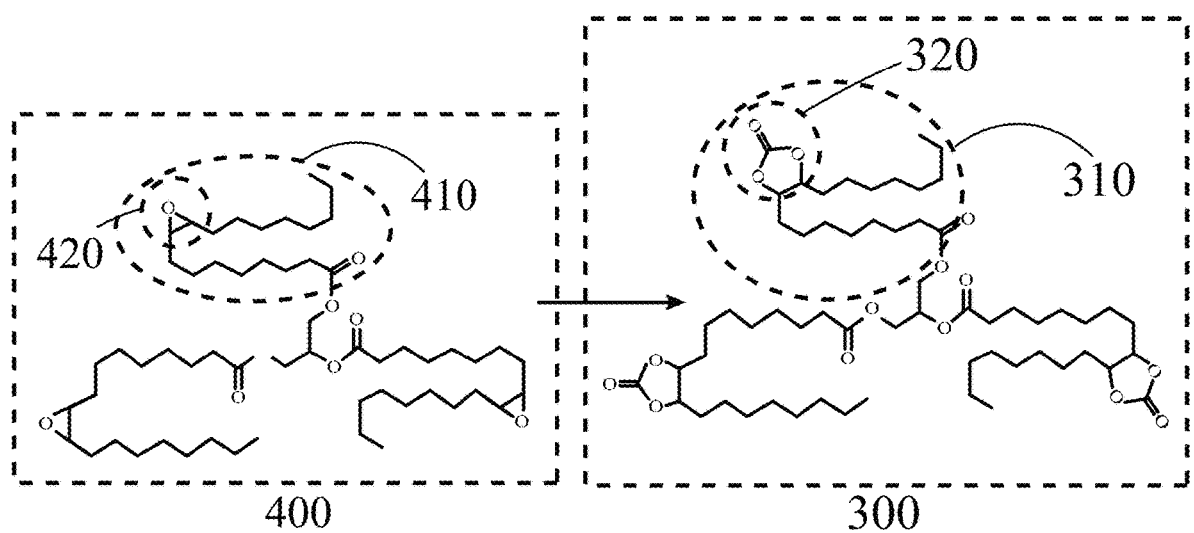
FIG. 4 illustrates a carbonation reaction of a lipid having at least one epoxy group on each fatty acyl chain to produce a lipid having at least one carbonate group, according to some embodiments of the present disclosure.
Figure 5:
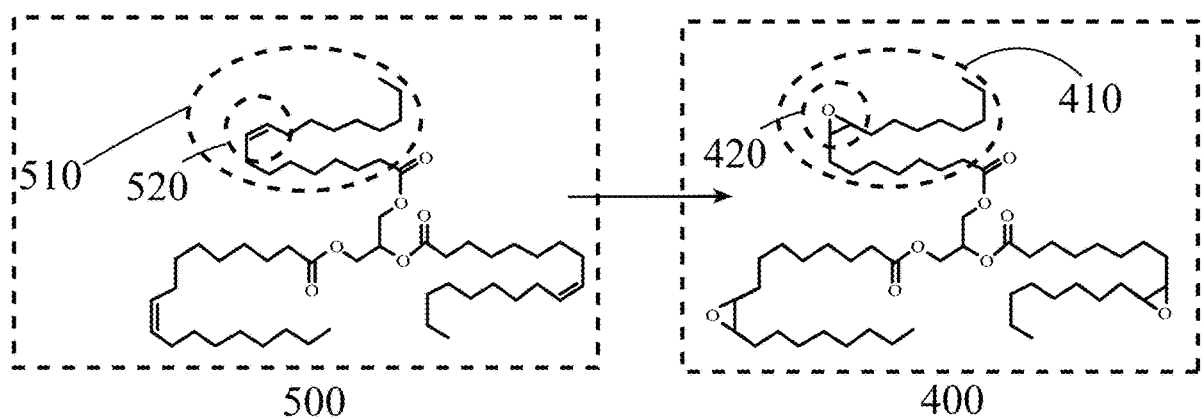
FIG. 5 illustrates an epoxidation reaction of a lipid having at least one carbon-carbon double bond on each fatty acyl chain to produce a lipid having at least one epoxy group, according to some embodiments of the present disclosure.

FIGS. 3, 4, and 5 illustrate how diamines, as described above, may be reacted with lipids/oils and/or lipid/oil derivatives, to form useful polymers and/or resins. As used herein, a polymer is defined as a mixture of long-chained molecules and a resin is defined as a mixture of long-chained molecules that are covalently linked by cross-linking molecules. FIG. 3 illustrates a molecule 330 (e.g. a polymer and/or a resin) formed by reacting a first lipid 300 with a diamine 110. In some embodiments of the present disclosure, the diamine 110 reacted with the first lipid 300 to form the polymer and/or resin 330 may include at least one of a diamine 110 formed by the decarboxylation of an amino acid and/or a diamine/polyamine formed by the reaction of a starting diamine with one or more amino acids such that the diamine 110 contains one or more peptide bonds. Referring again to FIG. 3, the first lipid 300 contains three fatty acyl chains 310 (only one of the three is labeled), with each fatty acyl chain 310 having at least one carbonate group 320. Thus, in some embodiments of the present disclosure, one of the amine functional groups of the diamine may react with one of the carbonate groups of the first lipid to produce a branched polymer. In some embodiments of the present disclosure, both amine functional groups of the diamine/polyamine may react with two carbonate groups of the first lipid to form a branched polymer. In some embodiments of the present disclosure, the amine functional groups of two or more diamines may react with two or more first lipids having carbonate groups to form a molecule that is a resin. For example, as shown in FIG. 3, four individual molecules of a first lipid 300 may react with three molecules of a diamine 110 (e.g. cadaverine) to produce a molecule 330 that includes the four molecules of the first lipid 300 covalently connected together by the cross-linking diamine 110 molecules.

In the example shown in FIG. 3, the first lipid 300 is a carbonated triacylglyceride (Carb TAG). In other words, the first lipid 300 shown in FIG. 3 includes three fatty acyl chains 310, each terminating with an ester group at a common, central carbon atom (marked by the asterisk). Thus, as used herein, a lipid may be any molecule having one or more fatty acyl chains with examples including monoacylglycerides, diacylgylcerides, triacylglycerides, and/or n-acylglycerides, phospholipid, glycolipid, hydroxyl fatty acid, fatty acid derivatives with ketone and aromatic groups where n is an integer value greater than one. Additional lipid molecule examples (e.g. oils) are fatty acid methyl esters, fatty acid ethyl esters, free fatty acids or glycerophospholipids, e.g. phosphatidylethanolamine, phosphatidyl choline, phosphatidyl inositol, etc. Additional molecules that may be used in some embodiments of the present disclosure are alkene compounds containing carbonate functional groups. Still further examples include polyunsaturated terpenes isoprene and myrcene, which may be produced by algae and/or plants.

The reactions shown in FIG. 3 may be generalized as follows:

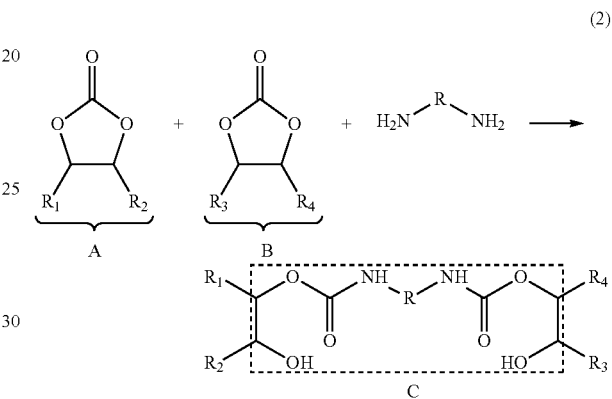

(2)

Thus, a first reactant A having at least one carbonate group, a first functional group $R_1$, and a second functional group $R_2$ may react with a second reactant B having at least one carbonate group, a third functional group $R_3$, and a fourth functional group $R_4$, and with a diamine to form a polymer and/or resin having at least one of functional group C (contained within the dashed outline). Thus, each functional group $R_1$, $R_2$, $R_3$, and/or $R_4$ may be the same or they may all be different functional groups, or there may be three groups that are the same, or two distinct pairs, etc. Each functional group $R_1$, $R_2$, $R_3$, and/or $R_4$ may include at least one of a saturated hydrocarbon chain and/or an unsaturated hydrocarbon chain, and these may be branched and/or straight chains. Further, each functional group $R_1$, $R_2$, $R_3$, and/or $R_4$ may include at least one of a carbonate group, a hydroxyl group, an amine group, an aryl group, an aromatic ring structures, a carboxyl group, ketone, and/or a sulfur-containing group. The number of carbonate groups included in each functional group $R_1$, $R_2$, $R_3$, and/or $R_4$ will determine whether relatively low molecular weight products are made (e.g. relatively few carbonate groups) or whether relatively high molecular weight products are made (e.g. relatively many carbonate groups). Similarly, the number of carbonate groups included in each functional group $R_1$, $R_2$, $R_3$, and/or $R_4$ will determine whether non-crosslinked polymers and/or molecules are made (e.g. zero and/or close to zero carbonate groups) are made or whether significantly cross-linked and/or branched resins are made (relatively many carbonate groups). Thus, in some embodiments of the present disclosure, at least one of the functional groups $R_1$, $R_2$, $R_3$, and/or $R_4$ will at least initially contain at least one carbonate group, which subsequently react with other diamine molecules to form additional C functional groups (e.g. linkages) as shown in above in Reaction 2, resulting in the formation of polymers and/or resins.

The first lipid 300 shown in FIG. 3 may be produced by the reaction shown in FIG. 4. FIG. 4 illustrates an example where the first lipid 300 is produced by converting a second lipid 400 having a fatty acyl chain 410 having an epoxy group 420. FIG. 5 illustrates an example wherein the second lipid 400 is produced by converting a third lipid 500 having a fatty acyl chain 510 having a carbon-carbon double bond 520.

Figure 6:
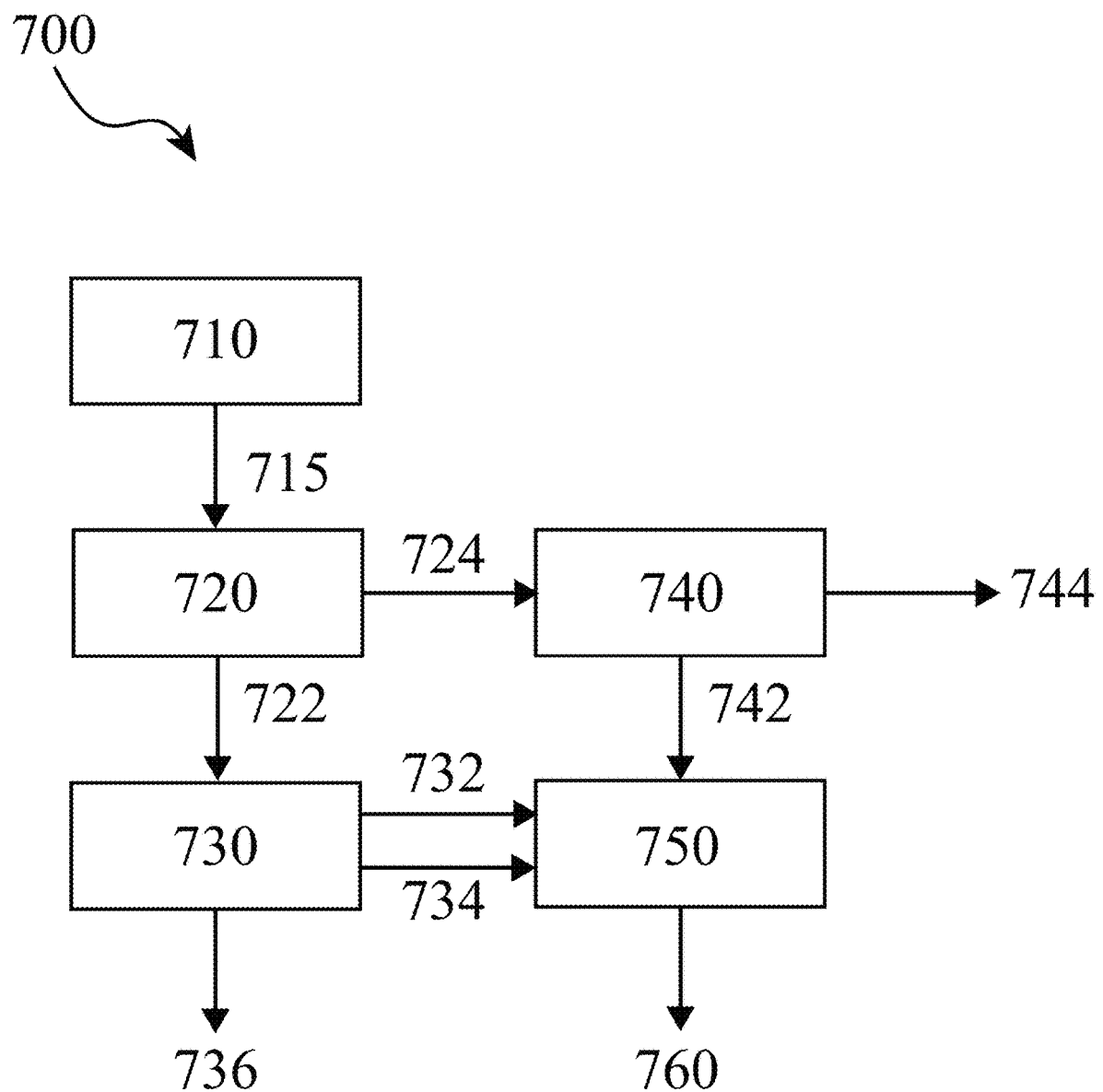
FIG. 6 illustrates a process for manufacturing polymers and/or resins as described herein, according to some embodiments of the present disclosure.

FIG. 6 illustrates an example of a process 700 for producing the polymers and/or resins described above. In general, the lipids, amino acids, peptides, and/or polypeptides used as starting materials to produce the polymers and/or resins may be bio-derived and/or petroleum-derived. The starting materials may be derived from a single source or from multiple sources. For example, amino acids, peptides, and/or polypeptides may be bio-derived while the lipids may be petroleum-derived. Similarly, bio-derived starting materials may be derived from a single source or multiple sources. For example, amino acid and lipid starting material may be derived from an algae source. Lipids and/or amino acids may be derived from canola seeds, soybeans, whey, meat, fermentation processes, organic waste sources (e.g. food, fats, oils and waste-grease, municipal solid and/or liquid waste), etc. Lipids may be derived from flax, soy, canola, corn, linseed, yeasts, fungi, algae, waste grease and/or fish. Thus, examples of sources for bio-derived starting materials include algae, fungi, bacteria, yeast, waste sources (municipal, food, agricultural), and/or plants. Examples of petroleum-derived and/or bioderived starting materials include alkenes with multiple double bonds, aliphatic polyesters and polyethers, derived from the polymerization of for example paraformaldehyde, polyethylene glycol (PEG) and polypropylene glycol (PPG) or polytetramethylene glycol (PTMG), or in the case of polyesters, the result of polycondensation of terephthalic acid and polyethylene glycol to form polyethylene terephthalate (PET) plastics, caprolactone forming polycaprolactone, or succinic acid and 1,4 butadiene to form polybutylene succinate (PBS), and/or 2,3-butanediol derived 1,3 butadiene and its diepoxy and dicarbonate derivatives.

The example process 700 shown in FIG. 6 is bio-derived specific. However, other embodiments that utilize non-biomass derived materials are considered to fall within the scope of the present disclosure. Thus, the process 700 of FIG. 6 begins with a biomass source 710 that supplies biomass 715 to a first separation unit 720. The biomass 715 may include a complex mixture of amino acids, oils, lipids, peptides, polypeptides and/or other common components. The first separation unit 720 may provide a first separation that, for example, separates mixture into at least an amino acid mixture 722 and a lipid mixture 724.

The amino acid mixture 722 may then be directed to a second separation unit 730 that separates the amino acid mixture 722 into one or more specific amino acid streams (732 and 734). Similarly, the lipid mixture 724 may be directed to a third separation unit 740 that separates the lipid mixture 724 into a saturated fatty acid stream 744 and an unsaturated fatty acid stream 742. In some embodiments of the present disclosure, the third separation unit 740 may include electrophoresis to separate the lipid mixture 724 into different, specific lipid components (see below). In some embodiments the present disclosure, the third unit 740 may include selective deoxygenation and distillation and therefore 744 may be an alkane stream produced from deoxygenation and distillation. Referring again to FIG. 6, in some embodiments of the present disclosure, the unsaturated fatty acid stream 742 and the amino acid streams (732 and 734) may be directed to an upgrading system 750 for converting these starting materials to useful polymers and/or resins as described above.

Figure 7:
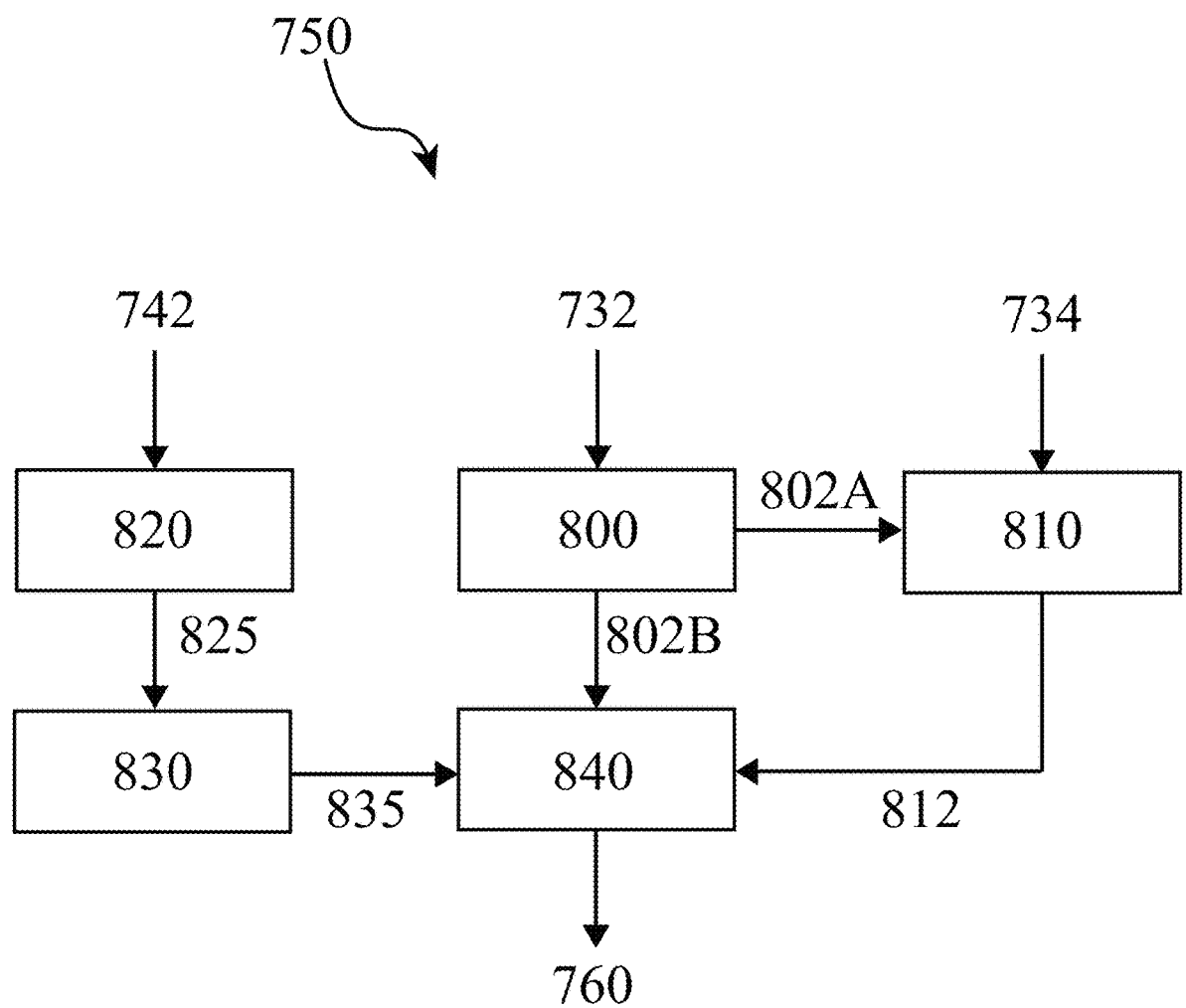
FIG. 7 illustrates a process for manufacturing polymers and/or resins as described herein, according to some embodiments of the present disclosure.

FIG. 7 provides more details regarding the upgrading system 750 and shows each of the unsaturated fatty acid stream 742, a first amino acid stream 732, and one or more additional amino acid streams 734 being directed to an epoxidation reactor 820, a decarboxylation reactor 800, and a cross-linker extension reactor 810, respectively. Thus, as shown in FIG. 5 and described above, the unsaturated fatty acid (e.g. unsaturated lipid) 742 may be converted to an epoxidized fatty acid 825 (e.g. epoxidized lipid), which may be subsequently directed to a carbonating reactor 830, wherein the epoxidized fatty acid 825 is converted to a carbonated fatty acid 835 (e.g. carbonated lipid) (see FIG. 4). As shown in FIG. 1 and as described above, the amino acid stream 732 may be decarboxylated in the decarboxylation reactor 800 to form diamine molecules. These resulting diamine molecules may be separated into a first diamine stream 802A, which may be directed to the cross-linker extension reactor 810 for subsequent reactions with the n$^{th}$ amino acid stream 734 according to the reactions summarized in FIG. 2 and described above. The upgrading system 750 shown in FIG. 7 then concludes by co-feeding the carbonated fatty acid 835 (e.g. the carbonated lipid), the diamine 802B, and the extended diamine 812 to a polymerization and/or resin reactor 840 for reacting these molecules according to the reaction shown in FIG. 3.

Figure 8:
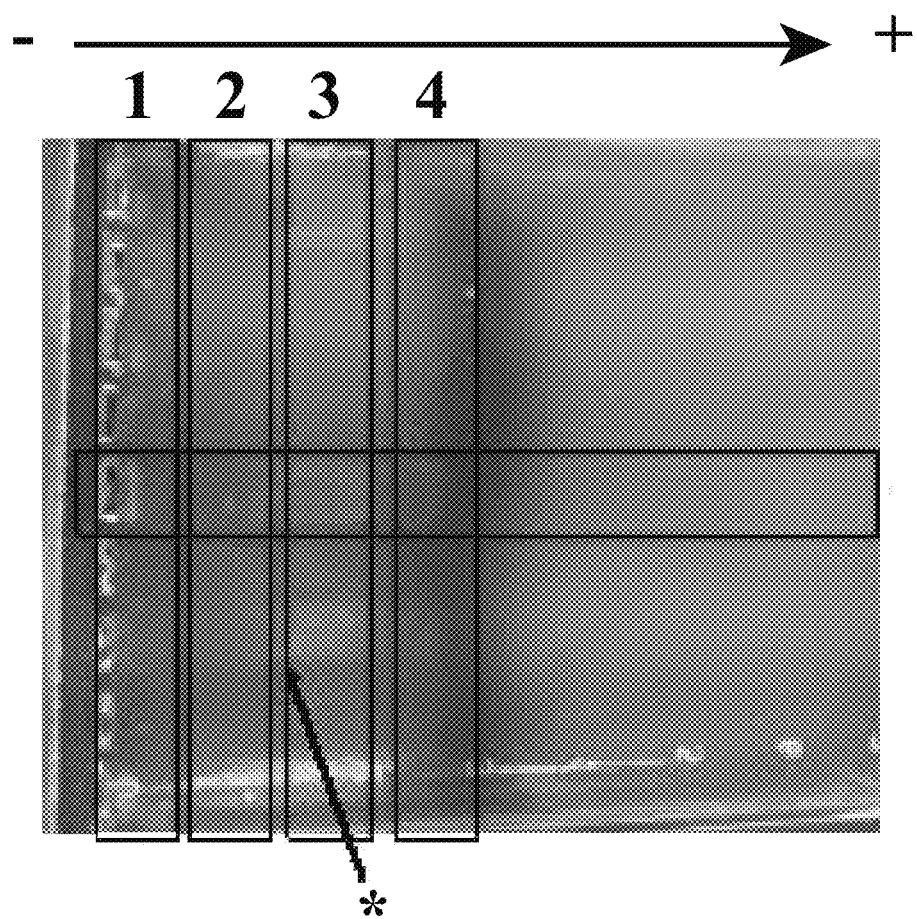
FIG. 8 illustrates the separation of lipids in electrophoretic system, according to some embodiments of the present disclosure.

Referring again to FIG. 6, in some embodiments of the present disclosure, the third separation unit 740 may include electrophoresis to separate a lipid mixture 724 into two streams; saturated oils oils/lipids/dienes/etc. from unsaturated oils/lipids/dienes/etc. To demonstrate the concept of enriching the level of unsaturated fatty acids in the oils used for polymerization with the goal of making the resulting oils more reactive in the polymer and/or resin synthesis process, oils from two feedstocks, menhaden fish oil and linseed oil (both rich in PUFA), were converted to water-soluble soaps to test the migration behavior under an electric field. The soaps prepared exhibited the identical fatty acid profile of the original oils and thus are adequate for studying the migration behavior and enrichment. Referring to FIG. 8, the respective soaps were loaded on an agarose gel, after which the gel was subjected to electrophoresis in an electrophoresis platform, after which the soaps visually migrated under the effect of the electric field (~50V), with the direction of the electric field indicated by the top horizontal arrow in FIG. 8. After 30 minutes of migration, the electrophoresis was stopped and the gel was separated into different fragments and analyzed for the fatty acid profile. Each of the samples was loaded onto the gel as three replicates and analyzed as distinct samples. Each replicate lane was cut into 4 fractions (see FIG. 8) and referred to as 1, 2, 3 or 4. The respective fatty acid profile indicates the contribution of each fatty acid measured to the total and in the original oils. The asterisked arrow indicates fatty acid soaps moving under the electric field and shows selective enriching for higher levels of unsaturation. The horizontally aligned rectangle indicates a replicate lane of menhaden fish oil soaps, cut into four fractions and subjected to the analysis described below. For the linseed preparation, over 95% of the fatty acids in the isolated fraction were PUFA, which is an enrichment not previously seen and supports the theory that electrophoresis or even the application of an electric field to oils can generate highly pure PUFA containing oils, with unprecedented composition and thus likely to open up new avenues of applications.

Figure 9:
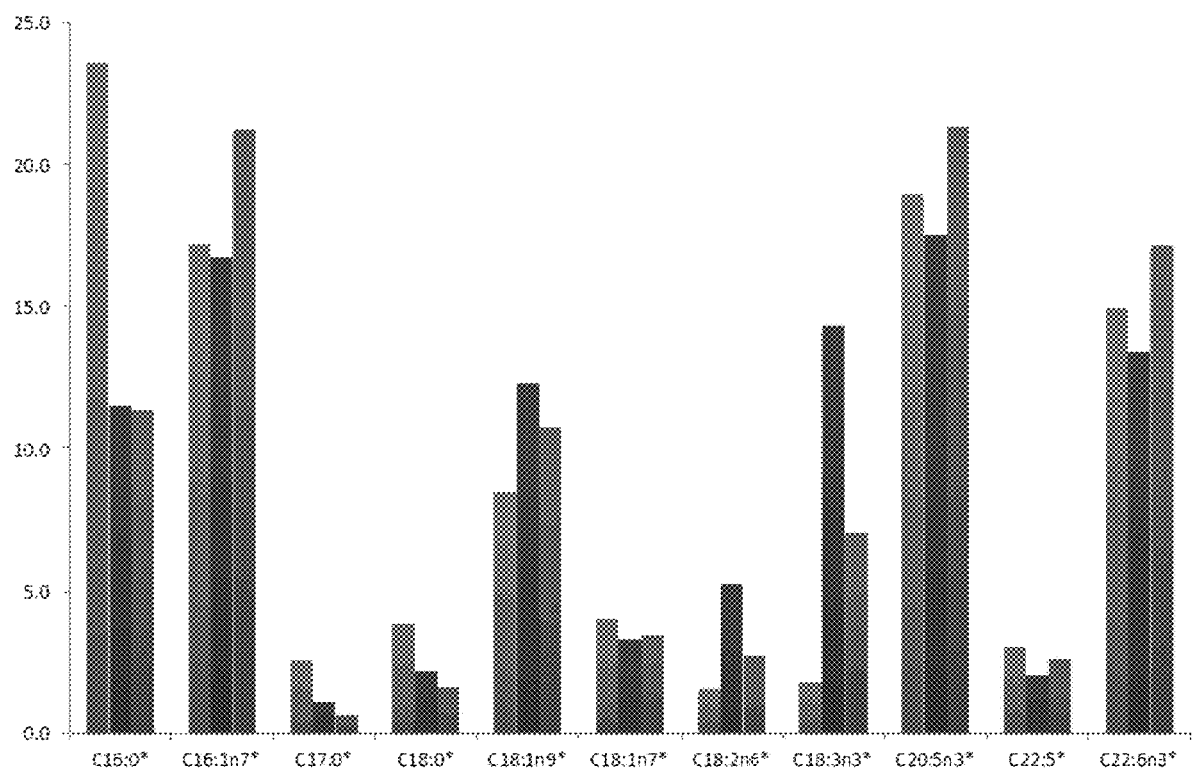
FIG. 9 illustrates PUFA enrichment in fraction 3 (see FIG. 8) isolated after separation under electrophoretic field relative to the menhaden fish oil original profile (left data sets), a reduction in saturated fatty acids (C16:0, C18:0) can be seen while an enrichment of PUFA, C20:5 and C22:6 is seen. Data is shown as the % contribution of the respective fatty acids to the total. Middle data sets=first replicate of enriched fraction; Right data sets=second replicate of enriched fraction.
Figure 10:
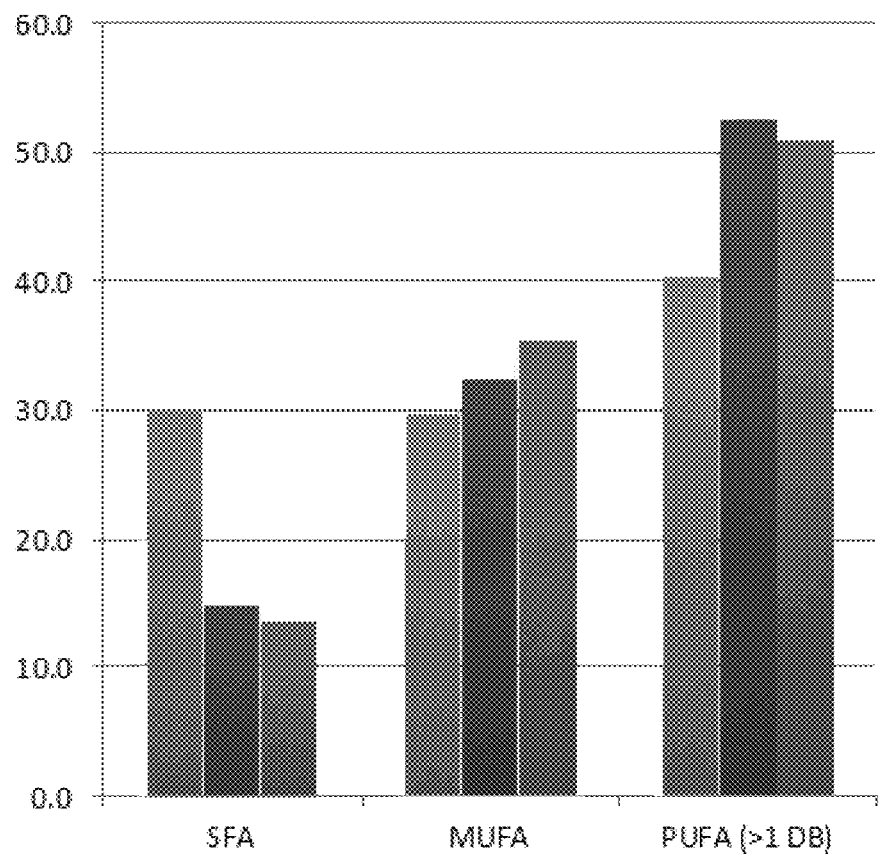
FIG. 10 illustrates the enrichment of PUFA in final menhaden fish oil fraction 3 relative to the original profile (left data sets), SFA=sum of saturated fatty acids, MUFA=sum of monounsaturated fatty acids, PUFA=sum of fatty acids with more than one unsaturated bond, with PUFAs exceeding 50% of the oils. Middle data sets=first replicate of enriched fraction; Right data sets=second replicate of enriched fraction.
Figure 11:
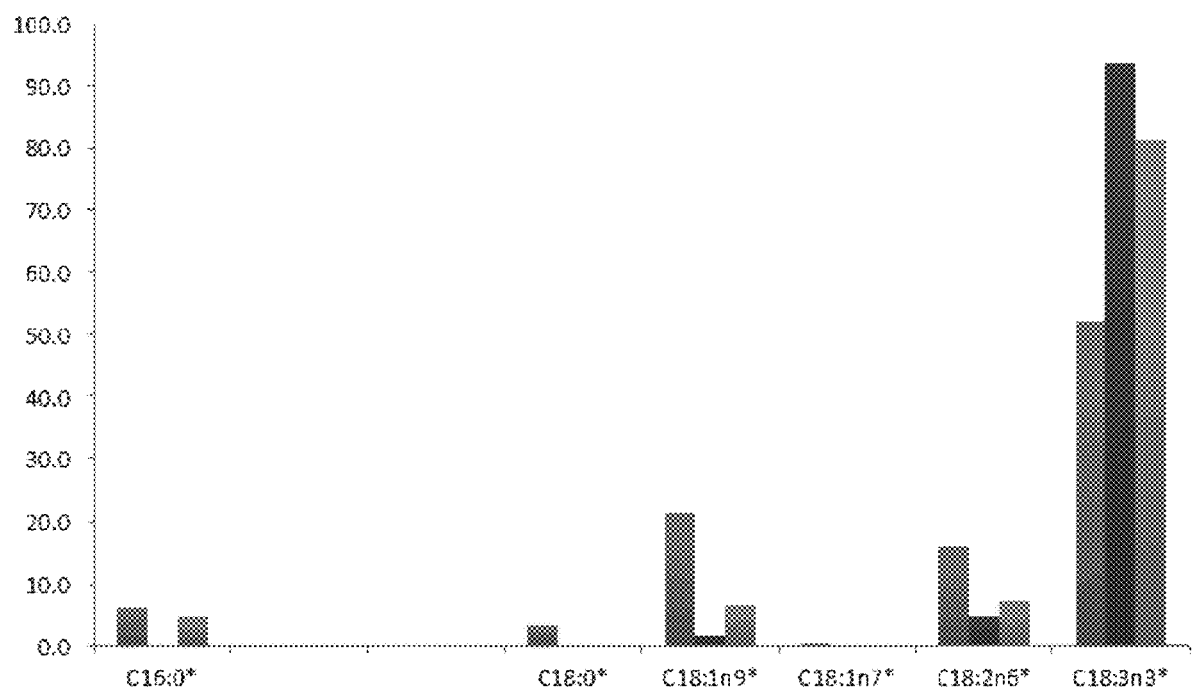
FIG. 11 illustrates a replicate PUFA enrichment in fraction 2 isolated after separation under electrophoretic field relative to the linseed oil original profile (left data sets), a reduction in saturated fatty acids (C16:0, C18:0) can be seen while an enrichment of PUFA, C18:3 concentrations exceeding 95% of all fatty acids is seen. Data is shown as the % contribution of the respective fatty acids to the total. Middle data sets=first replicate of enriched fraction; Right data sets=second replicate of enriched fraction.
Figure 12:
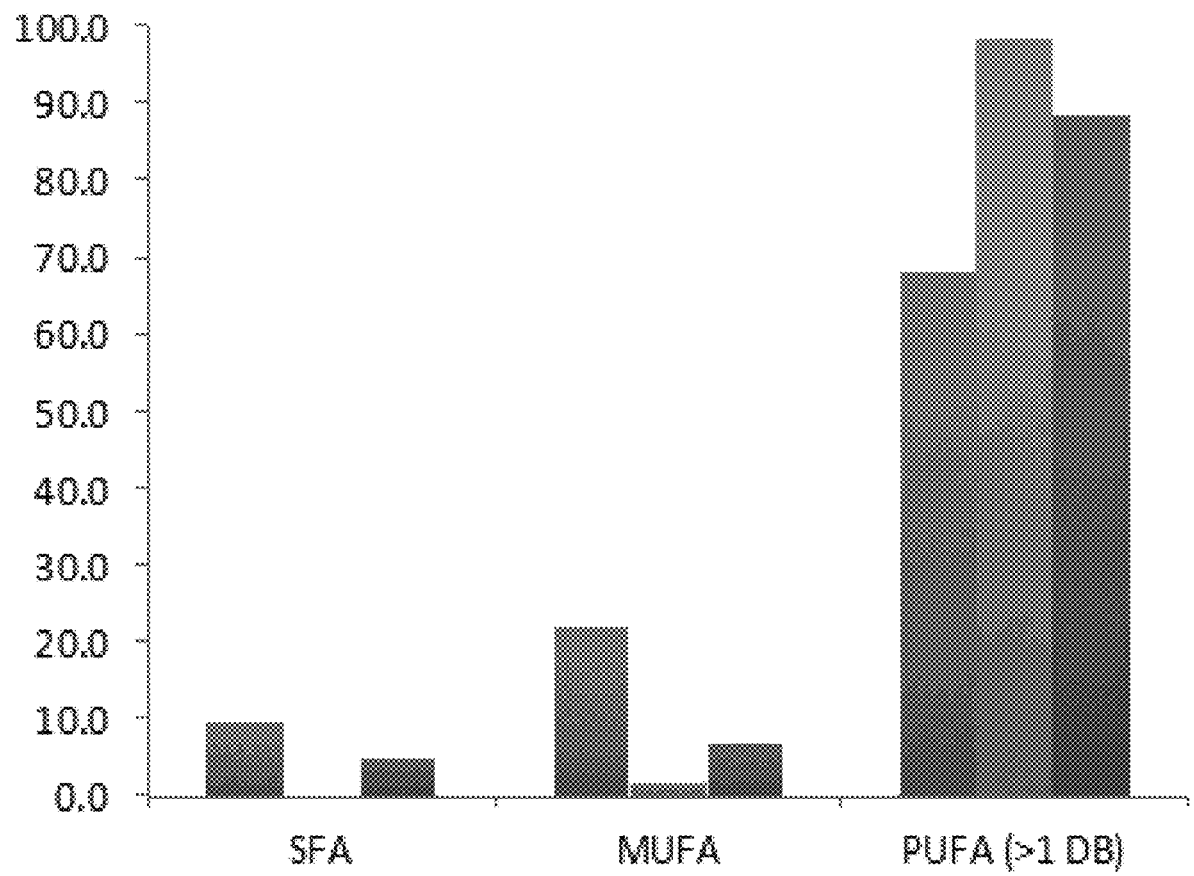
FIG. 12 illustrates the enrichment of PUFA in linseed oil fraction 2 relative to the original profile (left data sets), SFA=sum of saturated fatty acids, MUFA=sum of monounsaturated fatty acids, PUFA=sum of fatty acids with more than one unsaturated bond (enriched to >95% in fraction 2). Middle data sets=first replicate of enriched fraction; Right data sets=second replicate of enriched fraction.

FIGS. 9-12 summarize experimental data from experiments aimed at demonstrating the viability of electrophoresis from separating mixtures of lipids into various pure lipid streams. FIG. 9 illustrates fatty acid distribution of fish oil rich in polyunsaturated fatty acids (PUFA), such as C20:5n3 and C22:6n3, shown before and after electrophoresis enrichment. The increase in PUFA after enrichment indicates that a more reactive oil for polymers and/or resins may be prepared by migrating the oils or derived fatty acids in an electric field. This has direct benefits for separating out fatty acids and oil fractions from a bulk extract for polymer and/or resin synthesis, allowing for the remainder of the oils to be used for other applications such as fuel synthesis. FIG. 10 illustrates fatty acid distribution of fish oil rich in polyunsaturated fatty acids (PUFA), such as C20:5n3 and C22:6n3, summarized in categories of saturated fatty acids (SFA), monounsaturated fatty acids (MUFA) and PUFA, showing a distinct enrichment after electrophoretic migration of the fatty acids, creating a more reactive substrate for polymer and/or resin synthesis. FIG. 11 illustrates fatty acid distribution of linseed oil rich in polyunsaturated fatty acids (PUFA), such as C18:3n3, shown before and after electrophoresis enrichment, the increase in PUFA after enrichment indicates that a more reactive oil for polyurethane polymers can be prepared by migrating the oils or derived fatty acids in an electric field. FIG. 12 illustrates fatty acid distribution of linseed oil rich in polyunsaturated fatty acids (PUFA), such as C18:3n3, summarized in categories of saturated fatty acids (SFA), monounsaturated fatty acids (MUFA) and PUFA, showing a distinct enrichment after electrophoretic migration of the fatty acids, creating a more reactive substrate for polymer and/or resin synthesis. As used above, C20:5n3 refers to a hydrocarbon chain having an average number of 20 carbon atoms that includes 5 carbon-carbon double bonds, with the first bond at the third carbon position, with each successive carbon double bond alternating every third carbon position.

Figure 13:
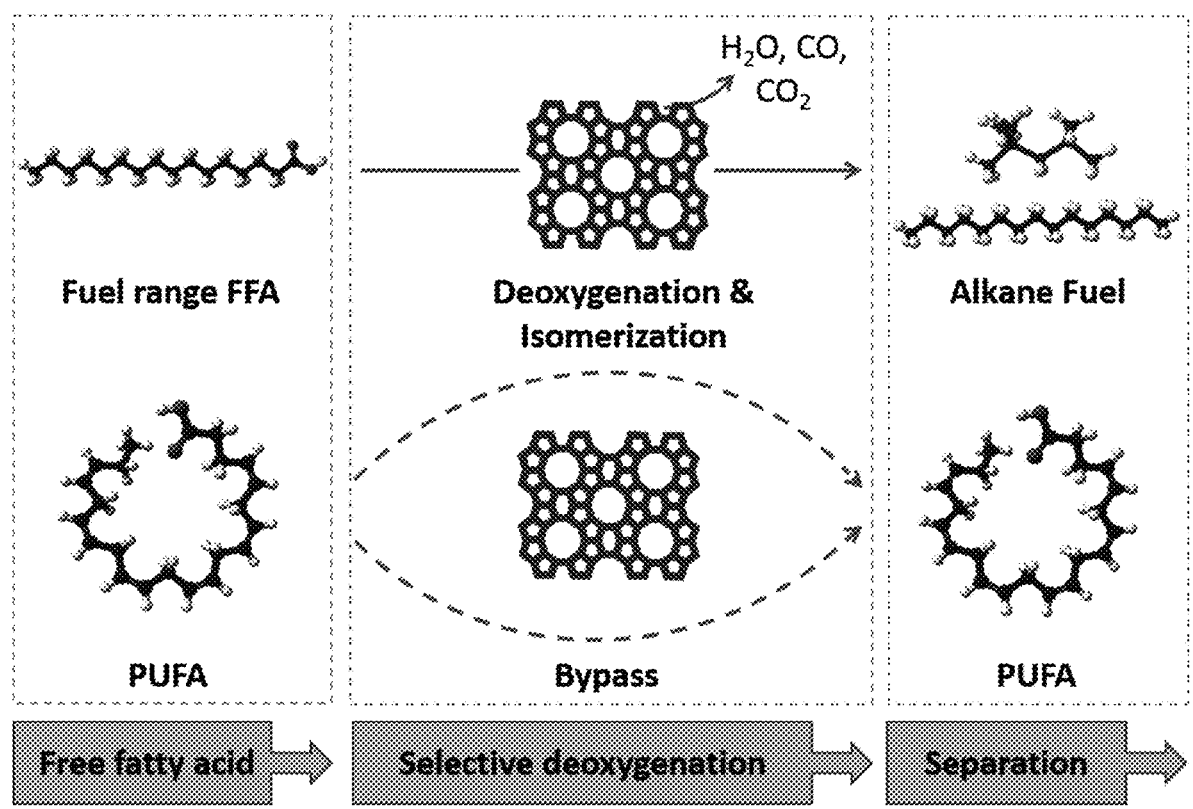
FIG. 13 illustrated the selective deoxygenation process using shape selective catalyst, according to some embodiments of the present disclosure.

As an alternative enrichment strategy, integrated with a fuel synthesis pathway, FIG. 13 illustrates a selective deoxygenation process using a shape selective catalyst, according to some embodiments of the present disclosure. Referring again to FIG. 6, in some embodiments of the present disclosure, the third separation unit 740 may include the process illustrated in FIG. 13 to separate a lipid mixture 724 into two streams; saturated oils oils/lipids/dienes/etc. from unsaturated oils/lipids/dienes/etc. In such a case, the third separation unit 740 may first start by passing lipid mixture 724 (containing saturated and unsaturated compounds) over a solid catalyst, which selectively (e.g. due to size exclusion using a zeolite) allows entry of the unsaturated compounds into the solid catalyst, wherein the unsaturated compounds are deoxygenated (e.g. decarboxylated) and/or isomerized to produce at least one of water, carbon monoxide, and/or carbon dioxide. However, the unsaturated compounds will simultaneously be excluded from entering the solid catalyst and retain their carbon-carbon double bonds and oxygen-containing functional groups (e.g. carboxylic acid groups). The resultant mixture of deoxygenated and/or isomerized saturated molecules (e.g. alkanes) may then be easily separated from the higher molecular weight, higher vapor pressure, unsaturated molecules by distillation. The resultant relatively pure alkane stream 744 may then by collected for use as fuel, whereas the resultant relatively pure unsaturated oil/lipid stream 742 may be diverted to used as a raw material in the reactions illustrated in FIGS. 3-5.

Additional Experimental Examples

Both epoxidized soybean oil and linseed oil were carbonated according to the reaction shown in FIG. 3. Table 2 below summarizes the physical property data for the starting epoxidized oils.

TABLE 2

Properties of epoxidized soybean oil and epoxidized linseed oil

| Chemicals | Epoxy oxygen content EOC % | Hydroxyl number OH#$^{TSI}$ (mg KOH/g) | Viscosity η@25° C. (Pa · s) |
|---|---|---|---|
| Epoxidized soybean oil (SO)* | 6.87 | 2.97 | 0.4 |
| Epoxidized linseed oil (LO)** | 9.49 | 4.79 | 0.8 |

Figure 14:
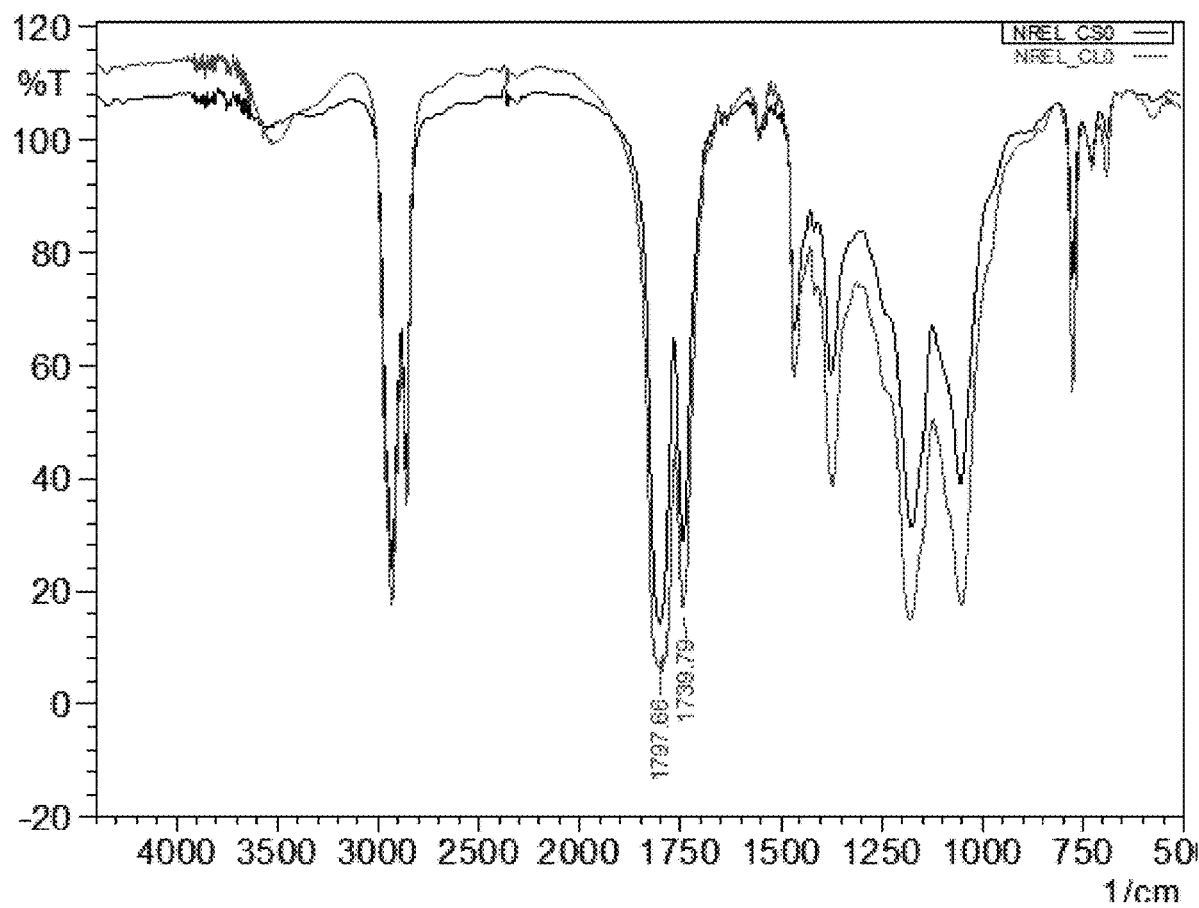
FIG. 14 illustrates Fourier Transform Infrared Spectroscopy (FTIR) spectra for two carbonated oils, according to some embodiment of the present disclosure.

The epoxidized soybean oil tested in this example was DRAPEX 6.85 from Chemtura and the epoxidized linseed oil tested in this example was EPDXOL 9.5 from ACS. Gel permeation chromatography (GPC) was performed on both epoxidized oil samples. GPC analysis of DRAPEX 6.85 showed a molecular weight distribution of about 94.09% triglycerides, about 2.45% of diglycerides, as well as small peak of 3.46% indicating the presence of higher molecular compounds. GPC analysis of EPDXOL 9.5 showed a molecular weight distribution of about 94.21% triglycerides, about 3.78% of diglycerides, as well as small peak of 2.01% indicating the presence of higher molecular weight compounds. Both of these oils, epoxidized soybean oil and epoxidized linseed oil, were carbonated according to the reaction shown in FIG. 4, using the following experimental procedure. For each case, the epoxidized oil and dried tetrabutylammonium bromide (0.05 moles) were placed in a 2000 mL, PM 8018 pressure reactor (PPI Pressure Products Industries) which was connected to a cylinder of carbon dioxide. The reaction mixture was stirred and heated to 110° C. and held for one hour. The mixture was then raised to 140° C. and 140 psi and maintained for a total of 24 hours with a moderate $CO_2$ flow for the entire reaction period. Liquid extraction was performed in a separatory funnel with EtOAc and water. The residual EtOAc/oil mixture was then washed three times with water. EtOAc was removed by rotary evaporation. The resultant carbonated oils were both a clear brown in color. FIG. 14 illustrates the Fourier Transform Infrared Spectroscopy (FTIR) spectra obtained for the two carbonated oils produced; CSO=carbonated soybean oil, CLO—carbonated linseed oil.

The carbonated soybean oil and carbonated linseed oil samples were than reacted according to the reaction shown in FIG. 3 to produce novel resins. The carbonated soybean oil was reacted with 1,4-diaminobutane, also referred to as putrescine and abbreviated herein as BDA, and in a separate reaction with 1,5-diaminopentane, also referred to as cadaverine and abbreviated herein as CA. Thus, the carbonated soybean oil was reacted with two separate diamine cross-linking molecules (BDA and CA) to form two separate resin products. The carbonated linseed oil was reacted with only one diamine cross-linking molecule, CA, to produce a single resin product. The starting formulations and reaction conditions for the resin synthesis reactions completed are summarized below in Table 3 for carbonate to amine ratios of 1:1.

TABLE 3

Resin Synthesis Formulations and Reaction Conditions

| Sample | CSO, g | CSO, eq | CLO, g | CLO, eq | Amine | Amine, g | Curing temperature, ° C. |
|---|---|---|---|---|---|---|---|
| CSO-BDA | 10 | 0.036 | — | — | BDA | 1.58 | 70 (15 hours) 100 (3 hours) |
| CSO-CA | 15 | 0.054 | — | — | CA | 2.75 | 70 (15 hours) 100 (3 hours) |
| CLO-CA | — | — | 15 | 0.070 | CA | 3.57 | 70 (15 hours) 100 (3 hours) |

Figure 15:
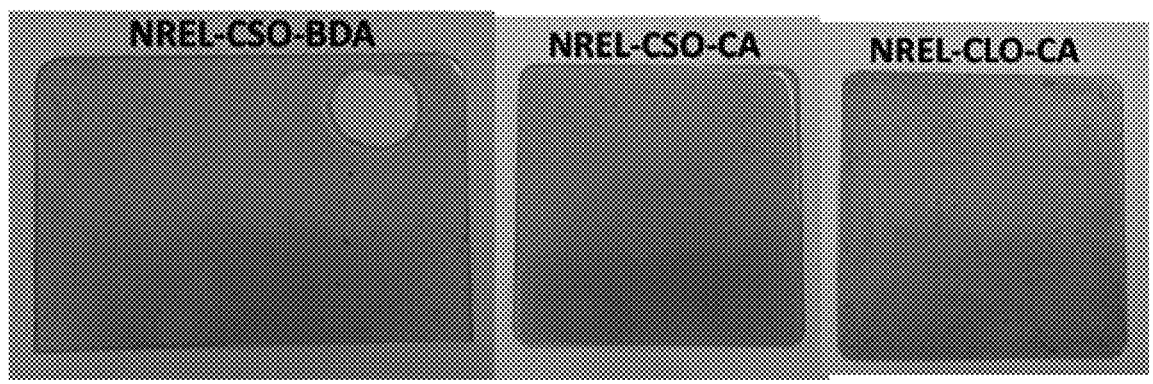
FIG. 15 illustrates photographs of three different resins produced according to the reaction summarized in FIG. 3, which include from left to right, reacting carbonated soybean oil (CSO) with 1,4-diaminobutate (BDA), reacting CSO with 1,5-diaminopentane (CA), and reacting carbonated linseed oil (LSO) with CA, according to some embodiments of the present disclosure

The resin synthesis reactions, according to FIG. 3, were completed as follows. Each respective carbonated oil was charged into a 50 ml Erlenmeyer flask equipped with magnetic stir bar and heated to 70° C. and kept under low vacuum for 30 minutes. The diamine was then injected along with strong stirring and continued heating. The mixture was stirred for around 5 minutes (just before significant viscosity rise) and transferred into a preheated mold at 70° C. The sample was then cured in oven at 70° C. for 15 hours and at 100° C. for 3 hours to produce the final resin product. FIG. 15 shows photographs of the resultant resin films.

Tables 4 through 7 summarize some physical property data measured from the resin samples made according to the procedure described above.

TABLE 4

Glass Transition Temperature Data

| Sample Name | Glass Transition Temperature (° C.) |
|---|---|
| NREL-CSO-BDA | −17.14 |
| NREL-CSO-CA | −17.21 |
| NREL-CLO-CA | 10.55 |

TABLE 5

Mechanical Integrity Data - Carbonated Soybean Oil Reacted with BDA

| Specimen number | Break Stress (MPa) | Break Elongation (%) | Place where spec. ruptures |
|---|---|---|---|
| spec 1 | 1.50 | 119 | Upper grip |
| spec 2 | 1.83 | 117 | Upper grip |
| spec 3 | 2.00 | 118 | Upper grip |
| MEAN | 1.78 | 118 | |

Note:
The width and thickness for the specimen was 7.8 mm and 1.1 mm

TABLE 6

Mechanical Integrity Data - Carbonated Soybean Oil Reacted with CA

| Specimen number | Break Stress (MPa) | Break Elongation (%) | Place where spec. ruptures |
|---|---|---|---|
| spec 1 | 1.96 | 116 | Middle |
| spec 2 | 1.63 | 113 | Bottom grip |
| spec 3 | 1.60 | 110 | Bottom grip |
| MEAN | 1.73 | 118 | |

Note:
The width and thickness for the specimen was 7.8 mm and 1.1 mm

TABLE 7

Mechanical Integrity Data - Carbonated Linseed Oil Reacted with CA

| Specimen number | Break Stress (MPa) | Break Elongation (%) | Place where spec. ruptures |
|---|---|---|---|
| spec 1 | 25.23 | 15 | Middle |
| spec 2 | 25.99 | 37 | Middle |
| spec 3 | 29.83 | 9 | Bottom grip |
| MEAN | 27.01 | 20 | |

Note:
The width and thickness for the specimen was 7.8 mm and 1.1 mm

In addition, examples of the reactions illustrated in FIG. 2 were also completed. Specifically, the amino acid lysine was reacted with decarboxylated lysine, cadaverine (CA), to produce a peptide and/or polypeptide diamine cross-linking molecule. This reaction may be generalized as follows:

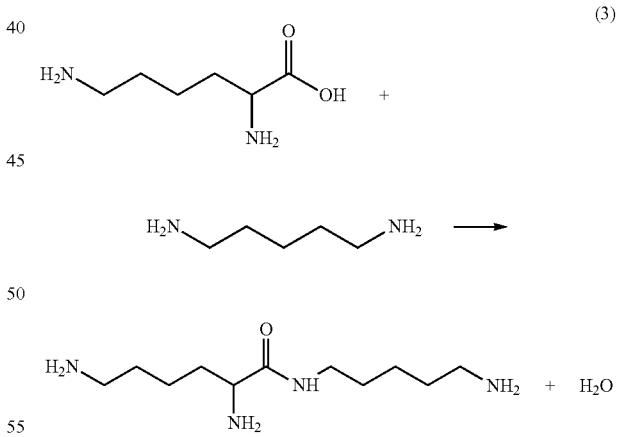

(3)

Reaction (3) to produce the diamine product was completed as follows. The lysine and cadaverine and NaOH were placed into 50 ml round bottom flask, equipped with air cooled reflux condenser, magnetic stir bar and nitrogen blanket. The mixture was heated and stirred at 110° C. for 20 hours. A final step that included the application of a high vacuum for 2 hours finished the reaction. Table 8 summarizes the properties of the resultant diamine product produced from Reaction (3).

TABLE 8

Diamine Data from Reacting Lysine with CA

| Sample | Calculated MW of amide | Number of amine groups | Equivalent MW per amide (calculated) | Amine Value (calculate) | Amine Value (measured) | Equivalen MW per amide (measured) |
|---|---|---|---|---|---|---|
| Lysine-CA | 231 | 3 | 77 | 729 | 813 | 69 |

In addition, the amino acid tyrosine was reacted with CA to produce another peptide and/or polypeptide diamine cross-linking molecule. This reaction may be generalized as follows:

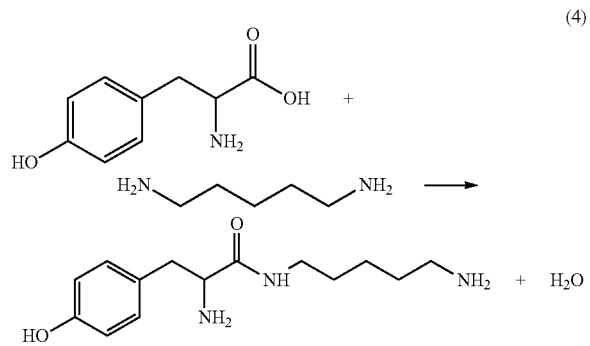

(4)

Reaction (4) to produce the diamine product was completed as follows. The tyrosine and cadaverine and NaOH were placed into 50 ml round bottom flask, equipped with air cooled reflux condenser, magnetic stir bar and nitrogen blanket. The mixture was heated and stirred at 110° C. for 20 hours. A final step that included the application of a high vacuum for 2 hours finished the reaction. Table 9 summarizes the properties of the resultant diamine product produced from Reaction (4).

TABLE 9

Diamine Data from Reacting Tyrosine with CA

| Sample | Calculated MW of amide | Number of amine groups | EW calculated | AmV calculated | AmV measured | EW measured |
|---|---|---|---|---|---|---|
| Tyrosine-CA | 266 | 2 | 133 | 422 | 285 | 197 |

In addition, resins according to the reactions shown in FIG. 3 were produced using carbonated linseed oil and the lysine-CA diamine cross-linker produced according to Reaction (3) and Table 8 above. The formulation used and starting conditions are summarized below in Table 10.

TABLE 10

Resin Synthesis Formulation and Reaction Conditions

| Sample | CLO, g | CLO, eq | Amine | Amine, g | Curing temperature, ° C. |
|---|---|---|---|---|---|
| CLO-Lys-CA | 9 | 0.042 | Lys-CA | 2.9 | 70 (18 hours) 100 (3 hours) |

Figure 16:
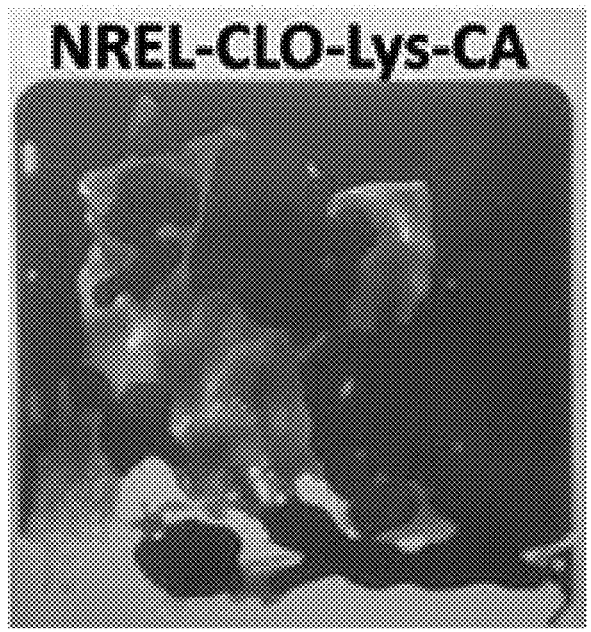
FIG. 16 illustrates a resin produced using a diamine cross-linking molecule obtained by reacting lysine with CA, followed by reacting the diamine with carbonated linseed oil, according to some embodiments of the present disclosure

The resin synthesis reaction, according to FIG. 3 and Table 10, was completed as follows. The carbonated linseed oil was charged into a 50 ml Erlenmeyer flask equipped with magnetic stir bar and heated to 70° C. and kept under low vacuum for 30 minutes. The diamine was then injected along with strong stirring and continued heating. The mixture was stirred for around 5 minutes (just before significant viscosity rise) and transferred into a preheated mold at 70° C. The sample was then cured in oven at 70° C. for 15 hours and at 100° C. for 3 hours to product the final resin product. FIG. 16 shows a photograph of the resultant resin film.

The resultant film had a glass transition temperature of about 21.6°. Table 11 summarizes mechanical integrity data for the resin obtained by reacting the lysine-CA diamine cross-linking molecule with carbonated linseed oil.

TABLE 11

Mechanical Integrity Data - Carbonated Linseed Oil Reacted with Tyrosine-CA Diamine

| Specimen number | Break Stress (MPa) | Break Elongation (%) | Place where spec. ruptures |
|---|---|---|---|
| spec 1 | 4.18 | 129 | Middle |
| spec 2 | 3.25 | 104 | Upper grip |
| spec 3 | 4.12 | 86 | Upper grip |
| MEAN | 3.85 | 106 | |

Finally, resins according to the reactions shown in FIG. 3 were produced using carbonated linseed oil and the tyrosine-CA diamine cross-linker produced according to Reaction (4) and Table 9 above. The formulation used and starting conditions are summarized below in Table 12.

TABLE 12

Resin Synthesis Formulation and Reaction Conditions

| Sample | CLO, g | CLO, eq | Amine | Amine, g | Curing temperature, ° C. |
|---|---|---|---|---|---|
| CLO-Tyr-CA | 4.14 | 0.0194 | Lys-CA | 2.2 | 70 (8 hours) |

Figure 17:
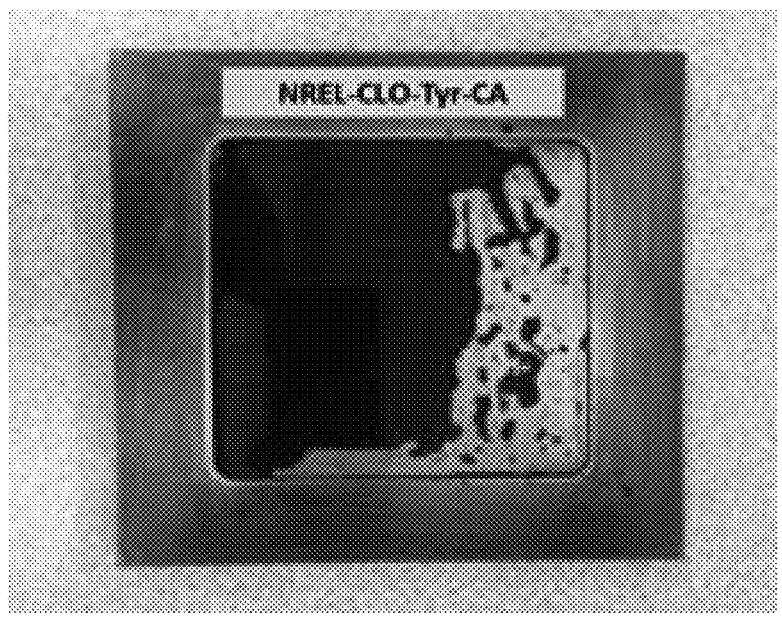
FIG. 17 illustrates a resin produced using a diamine cross-linking molecule obtained by reacting tyrosine with CA, followed by reacting the diamine with carbonated linseed oil, according to some embodiments of the present disclosure.

The resin synthesis reaction, according to FIG. 3 and Table 12, was completed as follows. The tyrosine-cadaverine diamide was dissolved in dimethylformamide (DMF). The carbonated linseed oil was charged into a 50 ml Erlenmeyer flask equipped with magnetic stir bar and heated to 70° C. and kept under low vacuum for 30 minutes. The diamine dissolved in DMB was then injected along with strong stirring and continued heating. The mixture was stirred for eight hours and transferred into a preheated mold at 110° C. The sample was then heated for seven days at atmospheric conditions to product the final resin product. FIG. 17 shows a photograph of the resultant resin film.

Additional Examples

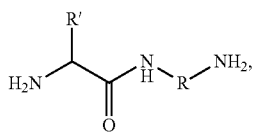

Example 1

A composition comprising: wherein: R is a first hydrocarbon group and R' is a second hydrocarbon group.

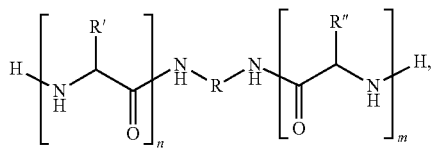

Example 2

The composition of Example 1, further comprising: wherein R" is a third hydrocarbon group.

Example 3

The composition of either Example 1 or Example 2, wherein R, R', and R" each comprises at least one of a saturated hydrocarbon chain or an unsaturated hydrocarbon chain having between 1 and 100 carbon atoms.

Example 4

The composition of any one of Examples 1-3, wherein the at least one of the saturated hydrocarbon chain or the unsaturated hydrocarbon chain comprises at least one of a branched chain or a straight chain.

Example 5

The composition of any one of Examples 1-4, wherein at least one of R' or R" further comprises at least one of a hydroxyl group, a carboxylic acid group, an amine group, a benzene ring, a phenol group, an amide group, an indol group, an imidazole group, a sulfhydryl group, or a guanidinium group.

Example 6

The composition of any one of Examples 1-5, wherein R' further comprises at least one of a hydroxyl group, a carboxylic acid group, an amine group, a benzene ring, a phenol group, an amide group, an indol group, an imidazole group, a sulfhydryl group, or a guanidinium group.

Example 7

The composition of any one of Examples 1-6, wherein R" further comprises at least one of a hydroxyl group, a carboxylic acid group, an amine group, a benzene ring, a phenol group, an amide group, an indol group, an imidazole group, a sulfhydryl group, or a guanidinium group.

Example 8

The composition of any one of Examples 1-7, wherein R comprises at least one of a —$CH_2$— group, an alkane, an alkene, or an alkyne.

Example 9

The composition of any one of Examples 1-8, wherein R comprises at least one of a straight chain or a branched chain.

Example 10

The composition of any one of Examples 1-9, wherein R further comprises at least one of a hydroxyl group, an amine group, an aryl group, an aromatic ring structure, a carboxyl group, ketone, or a sulfur-containing group.

Example 11

The composition of Example 1, comprising at least one of

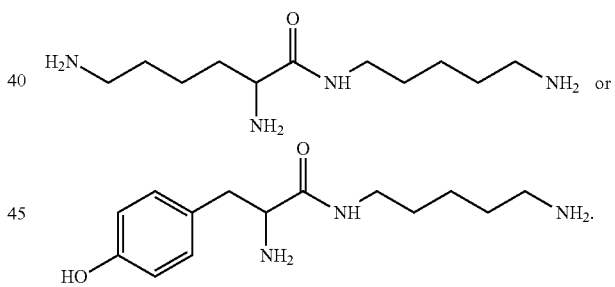

Example 12

A composition comprising:

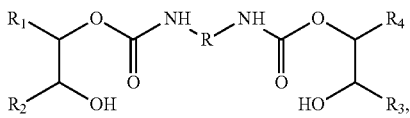

wherein: each of $R_1$, $R_2$, $R_3$, and $R_4$ comprises at least one of at least one of a hydrogen atom, a methyl group, a saturated hydrocarbon chain, or an unsaturated hydrocarbon chain, and R comprises at least one of a carbon atom, a saturated hydrocarbon chain, or an unsaturated hydrocarbon chain.

Example 13

The composition of Example 12, wherein at least one of $R_1$, $R_2$, $R_3$, and $R_4$ has between 1 and 100 carbon atoms.

Example 14

The composition of either Example 12 or Example 13, wherein at least one of $R_1$, $R_2$, $R_3$, and $R_4$ comprises at least one of a branched chain or a straight chain.

Example 15

The composition of any one of Examples 12-14, wherein the at least one of $R_1$, $R_2$, $R_3$, and $R_4$ comprises a saturated hydrocarbon chain having between 1 and 100 carbon atoms.

Example 16

The composition of any one of Examples 12-15, wherein the at least one of $R_1$, $R_2$, $R_3$, and $R_4$ comprises an unsaturated hydrocarbon chain having between 1 and 100 carbon atoms.

Example 17

The composition of any one of Examples 12-16, wherein R comprises at least one of a —$CH_2$— group, an alkane, an alkene, or an alkyne.

Example 18

The composition of any one of Examples 12-17, wherein R further comprises at least one of a straight chain or a branched chain.

Example 19

The composition of any one of Examples 12-18, wherein R further comprises at least one of a hydroxyl group, a carboxylic acid group, an amine group, a benzene ring, a phenol group, an amide group, an indol group, an imidazole group, a sulfhydryl group, or a guanidinium group.

Example 20

The composition of any one of Examples 12-19, wherein: R comprises

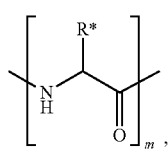

m is between 1 and 30, and R* comprises at least one of a hydrogen atom, a carbon atom, a methyl group, an alkane, an alkene, or an alkyne.

Example 21

The composition of any one of Examples 12-20, wherein R* further comprises at least one of a straight chain or a branched chain.

Example 22

The composition of any one of Examples 12-21, wherein R* comprises at least one of a hydroxyl group, a carboxylic acid group, an amine group, a benzene ring, a phenol group, an amide group, an indol group, an imidazole group, a sulfhydryl group, or a guanidinium group.

Example 23

The composition of any one of Examples 12-22, wherein: at least one of $R_1$, $R_2$, $R_3$, and $R_4$ further comprises a functional group A having the structure

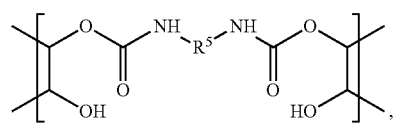

and $R^5$ comprises at least one of a —$CH_2$— group, an alkane, an alkene, or an alkyne.

Example 24

The composition of any one of Examples 12-23, wherein $R_1$ and $R_2$ have a combined total number of carbons between 10 and 30.

Example 25

The composition of any one of Examples 12-24, wherein the combined total number of carbons of $R_1$ and $R_2$ include between zero and ten of functional group A.

Example 26

The composition of any one of Examples 12-25, wherein $R_3$ and $R_4$ have a combined total number of carbons between 10 and 30.

Example 27

The composition of any one of Examples 12-26, wherein the combined total number of carbons of $R_3$ and $R_4$ include between zero and ten of functional group A.

Example 28

The composition of any one of Examples 12-27, wherein R comprises at least one of

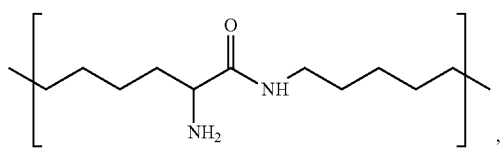

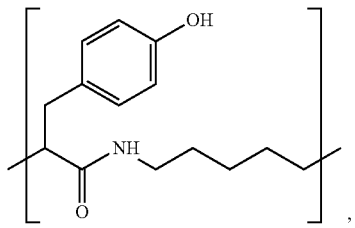

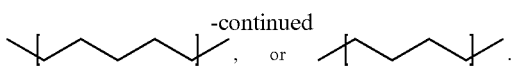

Example 29

The composition of any one of Examples 12-28, wherein: at least one of $R_1$, $R_2$, $R_3$, and $R_4$ further comprises a functional group A having the structure

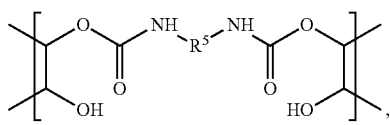

and
$R^5$ comprises at least one of a —$CH_2$— group, an alkane, an alkene, or an alkyne.

Example 30

The composition of any one of Examples 12-29, wherein $R_1$ and $R_2$ have a combined total number of carbons between 14 and 18.

Example 31

The composition of any one of Examples 12-30, wherein the combined total number of carbons of $R_1$ and $R_2$ include between zero and four of functional group A.

Example 32

The composition of any one of Examples 12-31, wherein $R_3$ and $R_4$ have a combined total number of carbons between 14 and 18.

Example 33

The composition of any one of Examples 12-32, wherein the combined total number of carbons of $R_3$ and $R_4$ include between zero and four of functional group A.

Example 34

The composition of any one of Examples 12-33, wherein the composition has a break stress between 1 MPa and 30 MPa.

Example 35

The composition of any one of Examples 12-34, wherein the break stress is between 1 and 2 MPa. (CSO with BDA or CA—Tables 5 and 6)

Example 36

The composition of any one of Examples 12-35, wherein the break stress is between 25 and 30 MPa. (CLO with CA—Table 7)

Example 37

The composition of any one of Examples 12-36, wherein the break stress is between 3 and 5 MPa. (CLO with Tyr-CA—Table 11)

Example 38

The composition of any one of Examples 12-37, wherein the composition has a break elongation between 5% and 140%.

Example 39

The composition of any one of Examples 12-38, wherein the break elongation is between 110% and 120%. (CSO with BDA or CA—Tables 5 and 6)

Example 40

The composition of any one of Examples 12-39, the break elongation is between 5% and 40%. (CLO with CA—Table 7)

Example 41

The composition of any one of Examples 12-40, the break elongation is between 80% and 140%. (CLO with Tyr-CA—Table 11)

Example 42

A method for producing polymers and resins, the method comprising: a first reacting of at least a first diamine with a first carbonate-containing compound and a second carbonate-containing compound to produce at least one of the polymer or the resin, wherein: the first reacting is according to

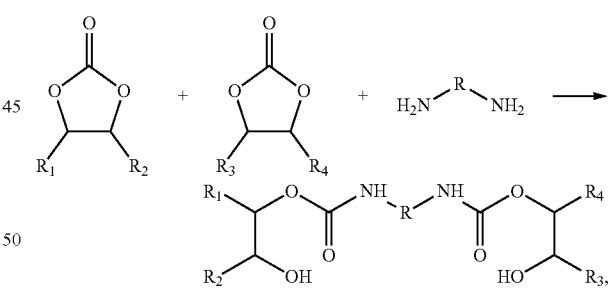

each of $R_1$, $R_2$, $R_3$, and $R_4$ comprises at least one of a hydrogen atom, a methyl group, a saturated hydrocarbon chain, or an unsaturated hydrocarbon chain, and R comprises at least one of a carbon atom, a saturated hydrocarbon chain, or an unsaturated hydrocarbon chain.

Example 43

The method of Example 42, further comprising, prior to the first reacting: a first carbonating of a first epoxide-containing compound to create the first carbonate-containing compound; and a second carbonating of a second epoxide-containing compound to create the second carbonate-containing compound.

Example 44

The method of either Example 42 or Example 43, further comprising, prior to the first carbonating or the second carbonating: a first epoxidizing of a first alkene-containing compound to create the first epoxide-containing compound; and a second epoxidizing of a second alkene-containing compound to create the second epoxide-containing compound.

Example 45

The method of any one of Examples 42-44, further comprising, prior to the first epoxidizing or the second epoxidizing: separating a first stream comprising a saturated hydrocarbon chain and an unsaturated hydrocarbon chain, wherein: the separating produces a second stream comprising substantially only the saturated hydrocarbon chain and a third stream comprising substantially only the unsaturated hydrocarbon chain, and the first alkene-containing compound and the second alkene-containing compound are contained in the third stream.

Example 46

The method of any one of Examples 42-45, wherein the separating is performed by size-exclusion utilizing a zeolite.

Example 47

The method of any one of Examples 42-46, wherein the separating is performed by electrophoresis.

Example 48

The method of any one of Examples 42-47, wherein the first stream is at least partially derived from biomass.

Example 49

The method of any one of Examples 42-48, wherein the biomass is derived from at least one of algae or plants.

Example 50

The method of any one of Examples 42-49, further comprising, prior to the first reacting: a second reacting of a first starting amine with a second starting amine to produce the first diamine, wherein: the second reacting is according to

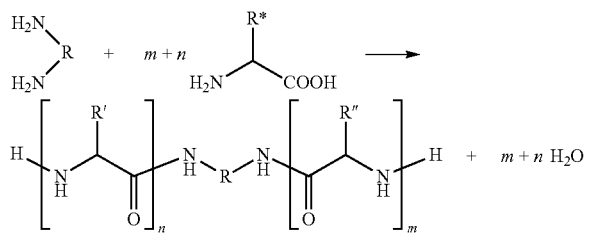

m is between 0 and 30, n is between 0 and 30, and at least one of the first starting amine or the second starting amine comprises an amino acid.

Example 51

The method of any one of Examples 42-50, wherein at least one of the first starting amine or the second starting amine comprises at least one naturally occurring amino acid.

Example 52

The method of any one of Examples 42-51, wherein at least one of the first starting amine or the second starting amine is derived from biomass.

Example 53

The method of any one of Examples 42-52, wherein the biomass is derived from at least one of algae or plants.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:
1. A composition comprising:
a compound having the formula

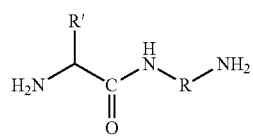

and a compound having the formula

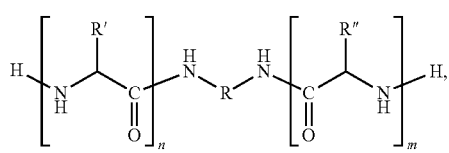

wherein:
R is derived from a naturally occurring amino acid having a carboxyl group, a first amine group, and a second amine group, and
R comprises a decarboxylated portion of the amino acid positioned between the first amine group and the second amine group,
R' is a first hydrocarbon group,
R" is a second hydrocarbon group,
n is between 2 and 30, inclusively, and
m is between 1 and 30, inclusively.

2. The composition of claim 1, wherein:
R' comprises a saturated hydrocarbon chain or an unsaturated hydrocarbon chain having between 1 and 100 carbon atoms, inclusively, and
R" comprises a saturated hydrocarbon chain or an unsaturated hydrocarbon chain having between 1 and 100 carbon atoms, inclusively.

3. The composition of claim 1, wherein
wherein R is

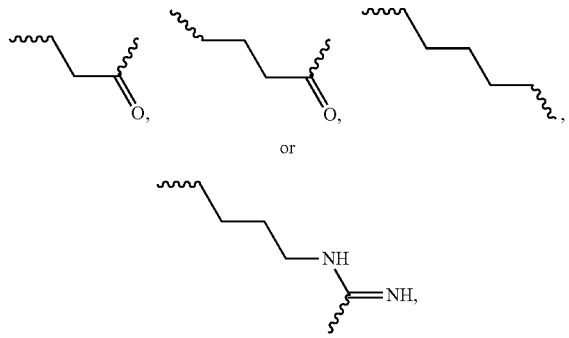

and
the symbol ⌇ represents covalent bond between R and a neighboring N atom.

4. A composition comprising:
a compound having the formula

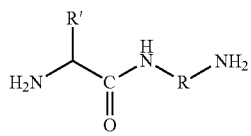

and a compound having the formula

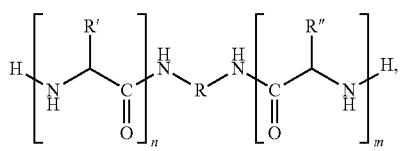

wherein:
R is

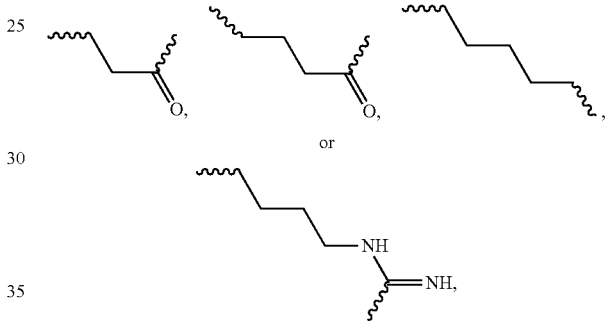

the symbol ⌇ represents a covalent bond between R and a neighboring N atom,
R' is a first hydrocarbon group,
R" is a second hydrocarbon group,
n is between 1 and 30, inclusively, and
m is between 1 and 30, inclusively.

* * * * *